(12) United States Patent
Ning et al.

(10) Patent No.: US 12,390,181 B2
(45) Date of Patent: Aug. 19, 2025

(54) CONE BEAM BREAST COMPUTED TOMOGRAPHY WITH PIVOTAL GANTRY SUBSYSTEM

(71) Applicant: Koning Corporation, Norcross, GA (US)

(72) Inventors: Ruola Ning, Atlanta, GA (US); Shaohua Liu, Atlanta, GA (US)

(73) Assignee: KONING CORPORATION, Norcross, GA (US)

( * ) Notice: Subject to any disclaimer, the term of this patent is extended or adjusted under 35 U.S.C. 154(b) by 0 days.

(21) Appl. No.: 18/914,218

(22) Filed: Oct. 13, 2024

(65) Prior Publication Data

US 2025/0032061 A1 Jan. 30, 2025

Related U.S. Application Data

(63) Continuation of application No. PCT/US2023/018382, filed on Apr. 12, 2023.

(60) Provisional application No. 63/430,571, filed on Dec. 6, 2022, provisional application No. 63/401,548, filed on Aug. 26, 2022, provisional application No. 63/401,475, filed on Aug. 26, 2022, provisional application No. 63/401,513, filed on Aug. 26, 2022, provisional application No. 63/401,546, filed on Aug. 26, 2022, provisional application No. 63/401,493, filed on Aug. 26, 2022, provisional application No. 63/331,153, filed on Apr. 14, 2022.

(51) Int. Cl.
| | | |
|---|---|---|
| A61B 6/00 | (2024.01) |
| A61B 6/03 | (2006.01) |
| A61B 6/04 | (2006.01) |
| A61B 6/40 | (2024.01) |
| A61B 6/50 | (2024.01) |
| A61B 8/08 | (2006.01) |
| G06T 7/00 | (2017.01) |

(52) U.S. Cl.
CPC .............. *A61B 6/502* (2013.01); *A61B 6/032* (2013.01); *A61B 6/035* (2013.01); *A61B 6/0435* (2013.01); *A61B 6/0478* (2013.01); *A61B 6/0487* (2020.08); *A61B 6/4085* (2013.01); *A61B 8/0825* (2013.01); *G06T 7/00* (2013.01); *G06T 2207/30068* (2013.01)

(58) Field of Classification Search
CPC ................................ A61B 6/025; A61B 6/032
See application file for complete search history.

(56) References Cited

U.S. PATENT DOCUMENTS

| | | |
|---|---|---|
| 6,987,831 B2 | 1/2006 | Ning |
| 10,603,003 B2 | 3/2020 | Bailey et al. |
| 11,191,502 B2 | 12/2021 | Smith |
| 11,478,206 B2 | 10/2022 | Smith et al. |
| 2005/0152501 A1 | 7/2005 | Sukovic |

(Continued)

OTHER PUBLICATIONS

Crotty, Dominic J. et al.; Investigating Novel Patient Bed Designs for Use in a Hybrid Dual Modality Dedicated 3D Breast Imaging System; Medical Imaging 2007: Physics of Medical Imaging; Proc. of SPIE vol. 6510, 65101H1-H10, (2007).

*Primary Examiner* — Dani Fox
(74) *Attorney, Agent, or Firm* — Bergman LLC; Michael Bergman

(57) ABSTRACT

A cone beam breast computed tomography scanning system includes a vertical plane gantry subsystem pivotally connected to a foundation element for ergonomic patient positioning.

9 Claims, 13 Drawing Sheets

(56) References Cited

U.S. PATENT DOCUMENTS

2012/0029338 A1 2/2012 Kuo et al.
2012/0069959 A1* 3/2012 Hoernig ............... A61B 6/0435
378/37

* cited by examiner

CONE BEAM BREAST COMPUTED TOMOGRAPHY WITH PIVOTAL GANTRY SUBSYSTEM

CROSS-REFERENCE TO RELATED APPLICATIONS

The present application is a continuation of PCT patent application PCT/US2023/018382 filed on Apr. 12, 2023, which claims the benefit of provisional patent applications OMNIBUS DISCLOSURE, set forth in an application for Letters Patent of the United States already filed on Apr. 14, 2022 as U.S. Provisional Application No. 63/331,153, and FIXTURING AND SUPPORT FOR MEDICAL IMAGING, set forth in an application for Letters Patent of the United States already filed on Aug. 26, 2022 as U.S. Provisional Application No. 63/401,475, and ERGONOMIC IMPROVEMENTS IN CONE BEAM BREAST COMPUTED TOMOGRAPHY, set forth in an application for Letters Patent of the United States already filed on Aug. 26, 2022 as U.S. Provisional Application No. 63/401,493, and STATIONARY DETAIL IMAGING IN CONE BEAM BREAST COMPUTED TOMOGRAPHY, set forth in an application for Letters Patent of the United States already filed on Aug. 26, 2022 as U.S. Provisional Application No. 63/401,513, and CONE BEAM BREAST COMPUTED TOMOGRAPHY WITH PATIENT SUPPORT SUBSYSTEM, set forth in an application for Letters Patent of the United States already filed on Aug. 26, 2022 as U.S. Provisional Application No. 63/401,546, and, CONE BEAM BREAST COMPUTED TOMOGRAPHY WITH PIVOTAL GANTRY SUBSYSTEM, set forth in an application for Letters Patent of the United States already filed on Aug. 26, 2022 as U.S. Provisional Application No. 63/401,548, and ULTRASONIC HYBRID IMAGING IN CONE BEAM BREAST COMPUTED TOMOGRAPHY, set forth in an application for Letters Patent of the United States already filed on Dec. 6, 2022 as U.S. Provisional Application No. 63/430,571, the disclosures of all of which are herewith incorporated by reference in their entireties.

FIELD OF THE INVENTION

The present invention relates to the field of cone beam tomographic imaging, and in particular to the field of patient ergonomics in cone beam breast tomographic imaging.

SUMMARY

According to the National Cancer Institute, one out of eight women will be diagnosed with breast cancer in her lifetime. And while a reduction in mortality from breast cancer is evident in published reports, each year 40,000 women will die of the disease.

The optimal breast imaging technique detects tumor masses when they are small, preferably less than 10 mm in diameter. It is reported that women with mammographically detected invasive breast carcinoma 1-10 mm in size have a 93% 16-year survival rate. In addition, as the diameter of the tumor at detection decreases, the probability of metastasis declines sharply. If a breast tumor is detected when it is 10 mm or less, the probability of metastasis will be equal to 7.31%. If a 4 mm carcinoma is detected, the metastatic probability will be decreased by more than a factor of 10, to 0.617%.

Although mammography, which on average can detect cancers about 12 mm in size, is the most effective tool for the early detection of breast cancer currently available, mammography has relatively low sensitivity to small breast cancers (under several millimeters). Specificity and the positive predictive value of mammography remain limited owing to structure and tissue overlap. The limited sensitivity and specificity in breast cancer detection of mammography are due to its poor contrast detectability, which is common for all types of projection imaging techniques (projection imaging can only have up to 10% contrast detectability), and mammography initially detects only 65-70% of breast cancers. The sensitivity of mammography is further reduced to as low as 30% in the dense breast. Digital mammography (DM) was developed to try to overcome the limitations inherent in screen-film mammography (SFM) by providing improved contrast resolution and digital image processing; however, a large-scale clinical trial, the Digital Mammographic Imaging Screening Trial (DMIST), showed that the rates of false positives for DM and SFM were the same.

The relatively low specificity of mammography leads to biopsy for indeterminate cases, despite the disadvantages of added cost and the stress it imposes on patients. Nearly 80% of the over one million breast biopsies performed annually in the U.S. to evaluate suspicious mammographic findings are benign, burdening patients with excessive anxiety and the healthcare system with tremendous cost. There is a need for more accurate characterization of breast lesions in order to reduce the biopsy rate and the false-positive rate of pre-biopsy mammograms.

The results of phantom studies indicate that Cone Beam Breast Computed Tomography (CBBCT) can achieve a spatial resolution up to about 2.8 lp/mm, allowing detection of a 2 mm carcinoma and microcalcifications about 0.2 mm in size for an average size breast (about 13 cm in diameter at the chest wall) with a total dose of about 5 mGy. This dose is less than that of a single mammography exam, assuming two views are required for each breast. The image quality of CBBCT for visualizing breast tissues, breast tumors and calcifications is excellent, and coverage of the breast, including the chest wall region, is at least equivalent to mammography. Visualization of major blood vessels is very good without using a contrast agent. Accordingly, CBBCT offers significant improvement in detecting and biopsying suspected lesions in a patient.

While the imaging benefits of CBBCT are remarkable, in many ways, the ergonomic advantages of the technology are just as important. For example, in many CBBCT procedures, an image can be acquired without requiring the compression of the breast tissue generally associated with mammography.

It is characteristic of mammography, for example, that breast imaging is preceded by insertion of a patient's breast into a fixturing apparatus that significantly compresses breast tissue in a direction transverse to a breast longitudinal axis. Patients widely report physical and psychological discomfort related to the degree of compression required for conventional mammography, and studies have shown that this discomfort is a contributing factor to low rates of screening and diagnostic mammography among patients generally and, in particular, among some ethnic and cultural populations.

Moreover, the breast compression associated with mammography can result in a displacement of breast tissue that makes the later localization of features such as lesions and calcifications, for purposes of biopsy and lumpectomy procedures, more difficult.

Additional improvements in CBBCT imaging presented herewith offer the potential to expand on its imaging benefits and offer ergonomic improvements that are likewise highly beneficial. Among these improvements are technical improvements, and methods and apparatus that facilitate presentation of the patient to the CBBCT system. These include loading apparatus, patient seating facilities, and equipment arrangements and configurations that improve comfort and ease of presentation of the patient to the machine for both the patient, and for technical and medical personnel.

In current practice, a patient undergoing CBBCT lies prone on a table. A subject breast is disposed downward through an aperture in an upper surface of the table, depending from the chest wall into an imaging chamber disposed under the table. The position of the breast within the imaging chamber is maintained by the patient remaining stationary as the patient lies on the surface of the table.

An imaging apparatus is coupled to a mobile gantry which is supported on a bearing device for rotation about an axis of rotation. The axis of rotation is disposed in a generally vertical orientation and passes through the aperture of the table. Preferably, an approximate centroid of the breast to be imaged is arranged such that the axis of rotation passes through the approximate centroid.

During imaging, the mobile gantry rotates around the axis of rotation, bringing the imaging apparatus through at least a portion of a circular path. As it traverses this path, the imaging apparatus emits a series of x-ray pulses and captures corresponding image data which is processed to prepare a tomographic model of the breast.

Notwithstanding the many benefits and advantages of CBBCT, there are some patients who find it difficult or impossible to assume a prone position on a patient table. Such patients may be unable to locate themselves properly on the table, or to dispose the breast to be imaged through the aperture as necessary. Patients who are elderly, obese, pregnant, or disabled, as well as those suffering from paralysis or amputation, among other ailments, are among the many for whom the act of climbing onto a table and lying down in a specific prone position is prohibitively difficult.

The inventors of the present invention, having given long and careful consideration to the problems associated with breast imaging, with CBBCT imaging and, in particular, to questions of CBBCT ergonomics, have developed new and useful systems, apparatus and methods that represent a substantial improvement over previously known approaches. The present invention includes apparatus, and corresponding systems and methods, for the entry of the patient into the CBBCT system, and for support of the patient during the tomographic imaging process.

Accordingly, in certain embodiments of the present invention, a CBBCT system is provided that is arranged for upright patient positioning. In certain embodiments of the invention, a patient is provided with a saddle for support during scanning in an upright position. In certain embodiments of the invention, the saddle is arranged to pivot so as to facilitate patient entry. In certain embodiments of the invention, the gantry is adapted to move pivotally away from a vertical orientation once a patient is positioned for scanning. In certain embodiments of the invention, the patient stands on a patient step without employing a saddle.

The following description is provided to enable any person skilled in the art to make and use the disclosed inventions and sets forth the best modes presently contemplated by the inventors of carrying out their inventions. In the following description, for purposes of explanation, numerous specific details are set forth in order to provide a thorough understanding of the present invention. It will be apparent to one skilled in the art, however, that the present invention may be practiced without these specific details. In other instances, well-known structures and devices are shown in block diagram form in order to avoid unnecessarily obscuring the substance disclosed. These and other advantages and features of the invention will be more readily understood in relation to the following detailed description of the invention, which is provided in conjunction with the accompanying drawings.

It should be noted that, while the various figures show respective aspects of the invention, no one figure is intended to show the entire invention. Rather, the figures together illustrate the invention in its various aspects and principles. As such, it should not be presumed that any particular figure is exclusively related to a discrete aspect or species of the invention. To the contrary, one of skill in the art will appreciate that the figures taken together reflect various embodiments exemplifying the invention.

Correspondingly, references throughout the specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" at various places throughout the specification are not necessarily all referring to the same embodiment. Furthermore, the particular features, structures, or characteristics will be combined in any suitable manner in one or more embodiments.

DETAILED DESCRIPTION

The following description is provided to enable any person skilled in the art to make and use the disclosed inventions, and sets forth the best modes presently contemplated by the inventors of carrying out their inventions. In the following description, for purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the substance disclosed.

It should be noted that while any of the embodiments described for exemplary purposes below will identify specific elements and combinations of elements, these examples are not intended to be determinative. Rather, discrete elements will, in appropriate circumstances, be combined into integral elements and/or assemblies. Further, the present disclosure of aspects and features of particular elements described herewith as integral, should be understood to convey also the disclosure of individual elements and assemblies providing the same characteristics and/or functionality.

Figure 1:
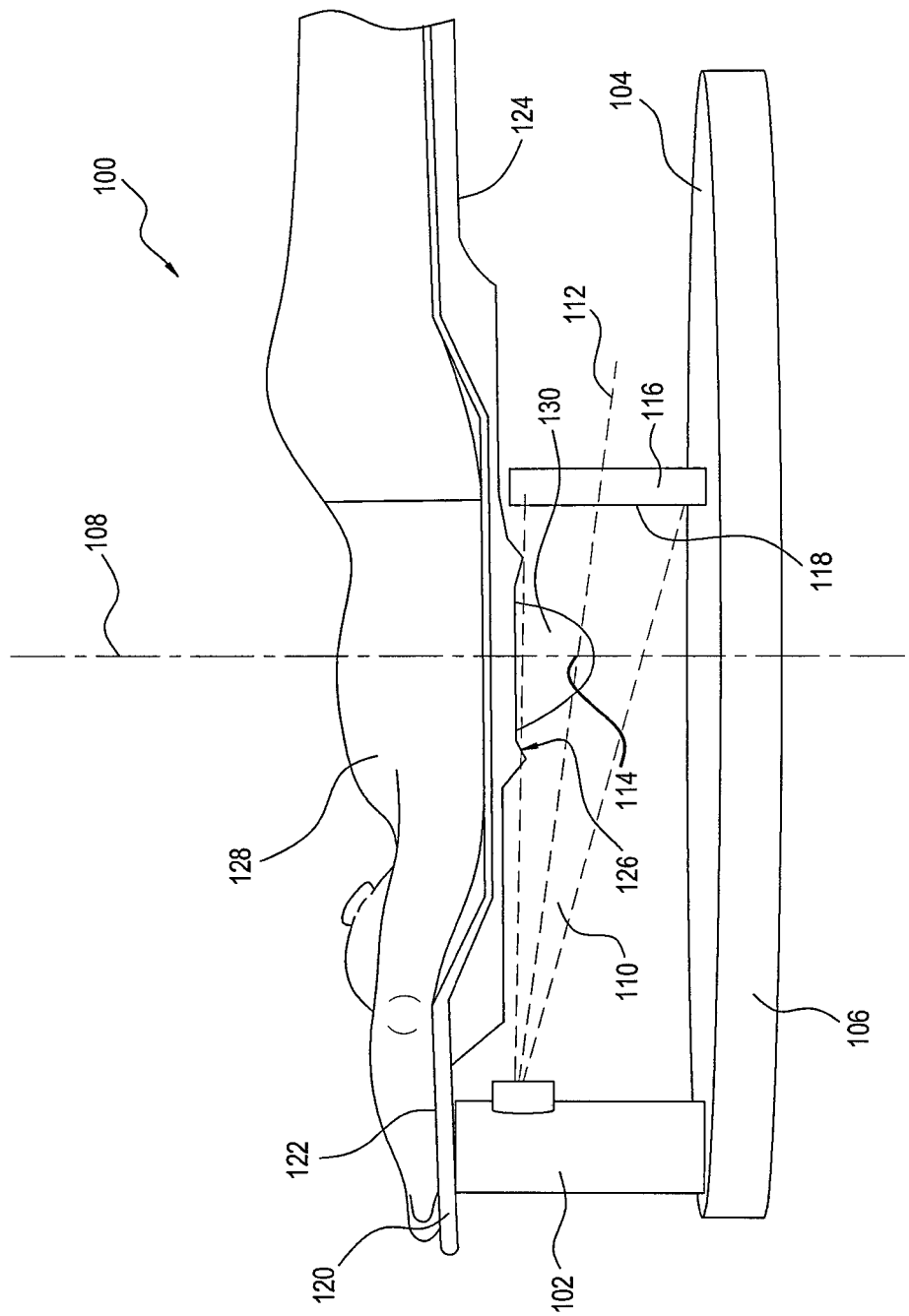
FIG. 1 shows, in cutaway perspective view, a portion of an exemplary CBBCT imaging system.

FIG. 1 shows, in cutaway perspective view, a portion of an exemplary CBBCT imaging system 100. The system 100 includes an x-ray source 102. The x-ray source 102 is mounted on an upper surface 104 of a rotating gantry 106. The rotating gantry 106 is supported by a bearing, and arranged for rotation about an axis of rotation 108.

The x-ray source 102 is configured to emit a beam of x-rays 110. The beam of x-rays 110 defines a beam longitudinal axis 112 that, in the illustrated embodiment, intersects (at 114) the axis of rotation 108.

In certain embodiments of the invention, beam 110 is configured as a cone beam. In certain configurations, a cross-section of the beam 110 taken transverse to the longitudinal axis 112 defines a disk of substantially uniform x-ray intensity with a substantially circular perimeter.

In other configurations within the scope of the invention, a cross-section of the beam 110 taken transverse to the longitudinal axis 112 defines a region of substantially uniform x-ray intensity with a substantially circular perimeter save for a portion of the disc outwardly of a chord of said circular perimeter. As will be appreciated on consideration of the further disclosure below, in certain embodiments, the chord will be disposed in generally parallel spaced relation to a lower surface of a patient table.

Accordingly, in certain configurations, a cross-section of the beam 110 taken transverse to the longitudinal axis 112 defines a truncated disk of substantially uniform x-ray intensity with a substantially truncated circular perimeter (i.e., a perimeter that is circular except for a horizontal chord of the circle at its upper periphery). This configuration optimizes imaging of the breast while minimizing irradiation of chest wall tissue above the breast. It is implemented, in certain embodiments, by the placement of an x-ray-opaque collimating plate across a portion of an otherwise circular-cross-section beam generated by the x-ray source.

In still further configurations within the scope of the invention, a cross-section of the beam 110 taken transverse to the longitudinal axis 112 defines a region of substantially uniform x-ray intensity with a polygonal perimeter, where the polygonal perimeter will, in respective embodiments and configurations, include any of a triangular perimeter, a rectangular perimeter, a pentagonal perimeter, hexagonal perimeter, a perimeter of any higher geometric shape, or a perimeter having any arbitrary curve or combination of line segments and curves according to the demands of a particular application. Moreover, it will be appreciated that any of the cross-sectional configurations described above may define a beam having a nonuniform intensity including, without limitation an intensity that falls to zero in a region, or certain regions, of the cross-section.

An x-ray detector 116 is also mounted on the upper surface 104 of the rotating gantry 106. In one exemplary embodiment, the x-ray detector 116 includes a flat panel detector having a generally planar receiving surface 118. Receiving surface 118 is disposed generally transverse to longitudinal axis 112 and on the opposite side of axis of rotation 108 from the x-ray source 102. It will be appreciated by one of skill in the art that the configuration described is merely exemplary of many possible arrangements in which the x-ray source, the x-ray detector, and any other component of the system, may be supported from above, from a side, or in any other way appropriate to achieving the desired function, and that the shape and configuration of the gantry, and of the x-ray detector, will likewise assume any appropriate form in respective embodiments of the invention.

Rotation of the gantry 106 about axis of rotation 108 during operation of the imaging system 100 will result in the receiving surface 118 following a transit path about axis of rotation 108. In a typical configuration, the transit path will include at least a portion of a circle disposed transverse to, and centered at, axis of rotation 108. It should be noted, however, that other transit paths are considered to be within the scope of the invention, and to be disclosed herewith.

In certain embodiments of the invention, one or both of the x-ray source 102 and the x-ray detector 116 are arranged so that their respective positions on the upper surface 104 of gantry 106 are adjustable. For example, the x-ray source 102 and the x-ray detector 116 may be adjustable in a radial direction with respect to axis of rotation 108, in a circumferential direction with respect to axis of rotation 108, in a direction towards or away from gantry surface 104, or in any other manner deemed beneficial by the designer or user of a particular apparatus embodying the invention.

A patient table 120 includes an upper surface 122 and a lower surface 124. An aperture 126 communicates between the upper surface 122 and lower surface 124 of the table. The upper surface 122 is arranged to support a patient 128, typically with the patient lying prone on the upper surface 122, as illustrated. In this arrangement, a breast 130 of the patient is disposed pendant from the patient's chest wall downwardly through aperture 126.

In operation, the gantry 106 rotates about axis of rotation 108, carrying x-ray source 102 and x-ray detector 116 in transit in a path around the patient's breast. During this transit, x-ray image data is captured by operation of the x-ray detector 116 in conjunction with corresponding interface electronics and computer systems. The x-ray image data corresponds to a plurality of x-ray images taken at respective angular locations about axis of rotation 108. Taken together, the x-ray image data, or a subset of the same, is processed to provide information about the internal state of the breast.

Figure 2A:
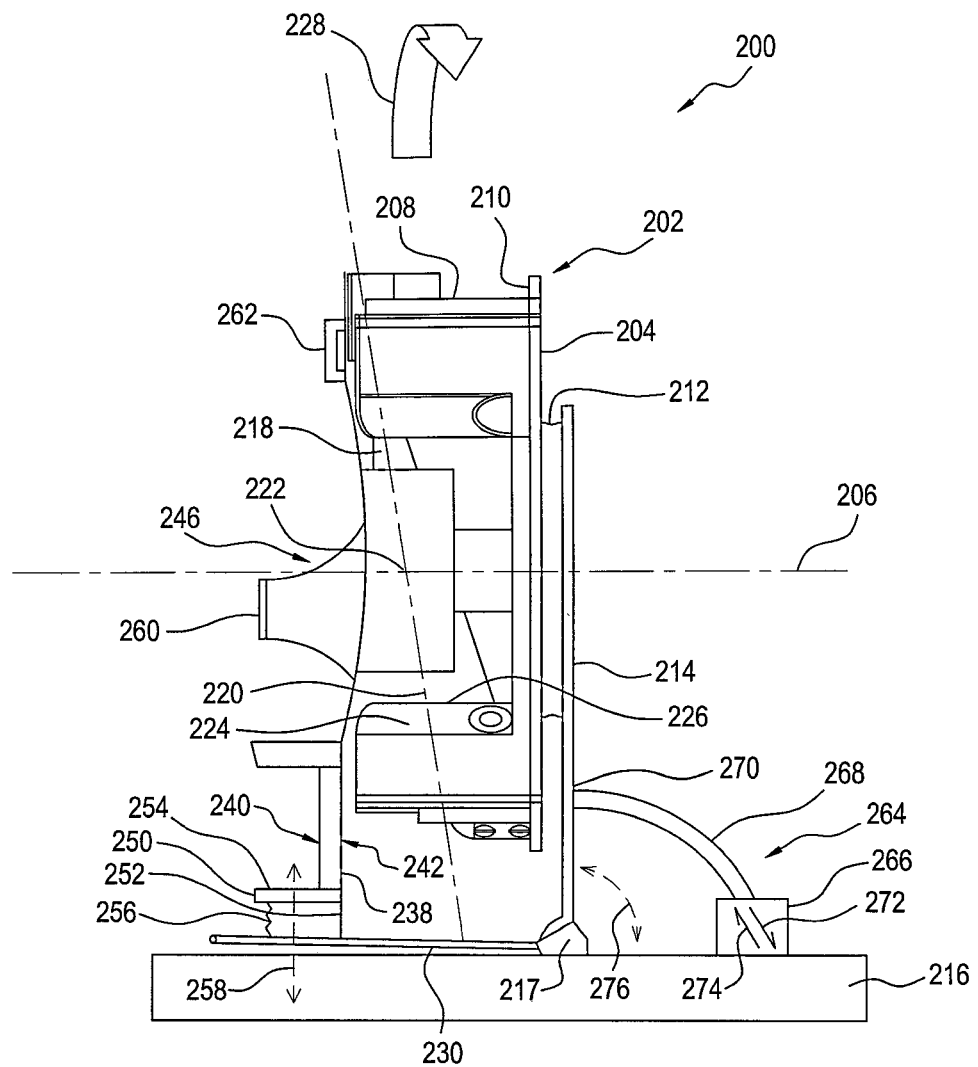
FIG. 2A shows, in schematic side elevation, certain aspects of an exemplary CBBCT imaging system, including a pivotable gantry subsystem prepared according to principles of the invention.

FIG. 2A shows, in schematic side elevation, a portion of an exemplary CBBCT imaging system 200, including a vertical plane gantry subsystem 202. The vertical plane gantry subsystem 202 includes a vertical plane gantry 204 configured to rotate about a generally horizontal axis of rotation 206.

Like system 100 described above, system 200 includes an x-ray source 208. The exemplary x-ray source 208 is mounted on, and supported by, a mounting surface 210 of the vertical plane gantry 204. The vertical plane gantry 204 is supported by a bearing 212, and arranged for rotation about the axis of rotation 206. The bearing 212 is, in turn, coupled to and supported by a structural member 214, and the structural member 214 is pivotally coupled to, and supported by, a foundation element 216 of the of the vertical plane gantry subsystem 202 at a hinge element 217.

The x-ray source 208 is configured to emit a beam of x-rays 218. The beam of x-rays 218 defines a beam longitudinal axis 220 that, in the illustrated embodiment, intersects (at 222) the axis of rotation 206.

In certain embodiments of the invention, beam 218 is configured as a cone beam of any appropriate cross-sectional configuration. As discussed above, the configuration and characteristics of the x-ray beam will be selected according to the requirements of a particular application.

An x-ray detector 224 is also mounted on the mounting surface 210 of the rotating gantry 204. In one exemplary embodiment, the exemplary x-ray detector 224 includes a flat panel detector having a generally planar receiving surface 226. Receiving surface 226 is disposed generally transverse to longitudinal axis 220 and on the opposite side of axis of rotation 206 from the x-ray source 208.

It will be appreciated by one of skill in the art that the configuration described is merely exemplary of many possible arrangements in which the x-ray source, the x-ray detector, and any other component of the system, may be supported from above, from a side, or in any other way appropriate to achieving the desired function, and that the shape and configuration of the gantry, and of the x-ray detector, will likewise assume any form in respective embodiments of the invention.

Rotation of the gantry 204 about axis of rotation 206 during operation of the imaging system 200 will result in the receiving surface 226 following a transit path 228 (as described above) about axis of rotation 206. In a typical configuration, the transit path will include at least a portion of a circle disposed transverse to, and centered at, axis of rotation 206. It should be noted, however, that other transit paths are considered to be within the scope of the invention, and to be disclosed herewith.

In certain embodiments of the invention, one or both of the x-ray source 208 and the x-ray detector 224 are arranged so that their respective positions on the mounting surface 210 of gantry 204 are adjustable. For example, the x-ray source 208 and the x-ray detector 224 may be adjustable in a radial direction with respect to axis of rotation 206, in a circumferential direction with respect to axis of rotation 206, in a direction towards or away from gantry surface 210, in an angular orientation, or in any other manner deemed beneficial by the designer or user of a particular apparatus embodying the invention.

A base member 230 is coupled to the structural member 214. A patient interface panel 238 is coupled through the base member 230 to the structural member 214 so that the structural member 214 and the base member 230 serve to support the patient interface panel 238.

The patient interface panel 238 has a first patient interface surface region 240 and a second distal surface region 242, where the distal surface region 242 is disposed in spaced relation to the patient interface surface region 240. The exemplary patient interface panel functions to segregate the patient from the moving apparatus of the vertical plane gantry subsystem and provides an aperture for the breast.

Figure 2B:
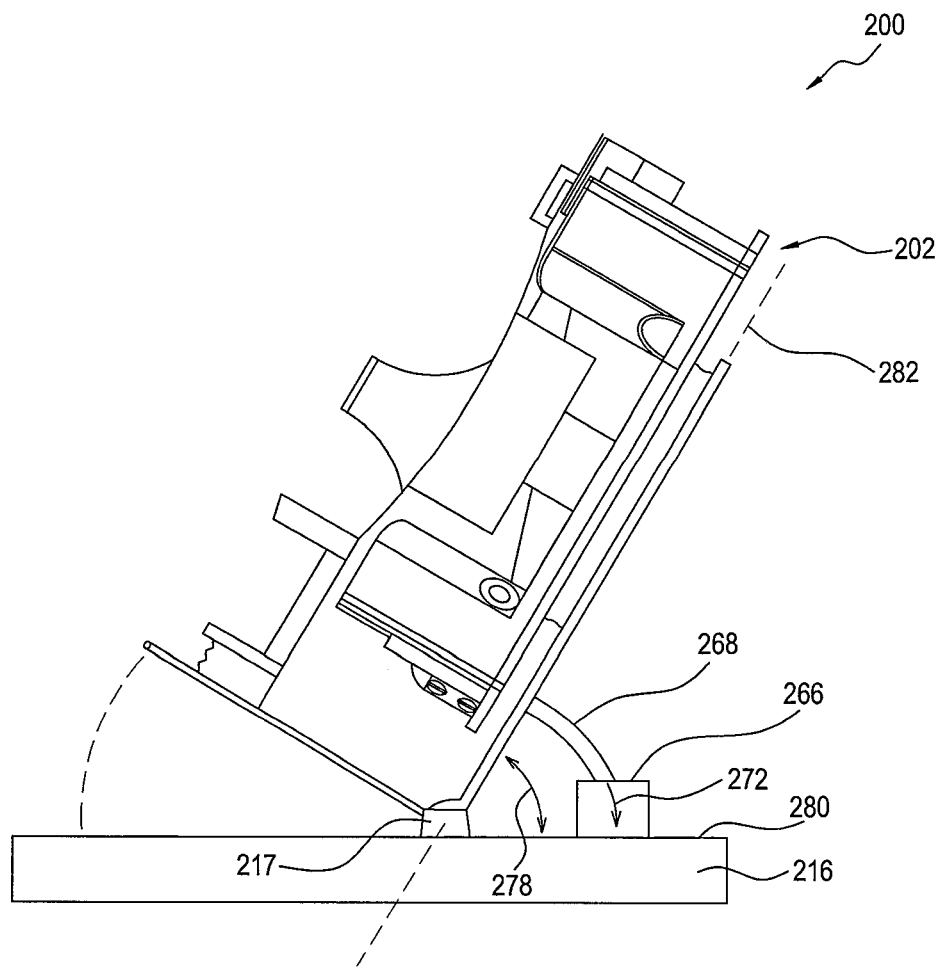
FIG. 2B shows, in schematic side elevation, additional aspects and configurations of an exemplary CBBCT imaging system, including a pivotable gantry subsystem prepared according to principles of the invention.

Accordingly, referring to FIGS. 2A and 2B the patient interface panel includes an internal circumferential edge of the patient interface surface region. The internal circumferential edge circumscribes an aperture 246 through the patient interface panel 238 between patient interface surface region 240 and distal surface region 242.

As will be further described below, the patient interface surface region 240 is arranged to segregate the patient from the balance of the vertical gantry subsystem 202 with a breast of the patient disposed through the aperture 246. In various embodiments and aspects of the invention, a patient interface subsystem, as exemplified above, is disposed at the aperture 246. In various aspects, the patient interface subsystem will provide one or more of an aperture sized and located according to the particular patient and breast being imaged, shielding for regions of the patient that might otherwise be exposed to scattered x-ray photons, and support and stabilization of the breast being imaged, among other features.

In operation, the gantry 204 rotates about axis of rotation 206, carrying x-ray source 208 and x-ray detector 224 in a transit path 228 around the patient's breast. During this transit, x-ray image data is captured by operation of the x-ray detector 224 in conjunction with corresponding interface electronics and computer systems. The x-ray image data corresponds to a plurality of x-ray images taken at respective angular locations about axis of rotation 206. Taken together, the x-ray image data, or a subset of the same, is processed to provide information about the internal state of the breast.

In certain embodiments of the invention, a patient step 250 is provided adjacent a lower surface region 252 of the patient interface panel 238. The patient step 250 has an upper surface region 254. The upper surface region 254 is configured and adapted to support a patient during imaging.

In certain embodiments of the invention, the patient step 250 is coupled to and supported by an adjustment mechanism 256. Adjustment mechanism 256 is, in respective embodiments of the invention, coupled to base member 230, or to patient interface panel 238, or otherwise coupled to the CBBCT imaging system 200 for support.

In certain embodiments of the invention, adjustment mechanism 256 is arranged and configured to provide adjustable positioning, e.g., in direction 258, with respect to the patient interface surface region 240 of patient interface surface panel 238. Accordingly, the adjustment mechanism serves to optimize positioning of a patient, according to a patient's height and dimensions, with respect to aperture 246 for effective imaging of the subject breast.

According to certain aspects of the invention, patient parameters (such as e.g., breast height with respect to patient feet) are secured, either by manual measurement of the patient, by extraction from patient medical records, or by automatic measurement. The parameter values, once secured, are optionally used to set the position of the patient step, adjusting its elevation in direction 258 and its orientation. The patient then mounts the patient step 250 and leans into the patient interface surface 240 of the patient interface panel 238.

Alternately, in certain embodiments of the invention, the patient steps onto the patient step. Thereafter, the height and orientation of the patient step are adjusted with the patient disposed in situ, and the necessary positioning (i.e., patient parameters) are ascertained from manual observation or automatic sensing of the patient body with respect to the system. In other words, the patient step is adjusted until the patient breast is properly situated within the table aperture.

In certain embodiments of the invention, the adjustment mechanism 256 will include one or more of a scissors link mechanism, or a linear bearing mechanism, along with any of the linear actuators identified below, or any other elevating mechanism consistent with the objectives of the invention, such as would become apparent to one of skill in the art in light of the requirements of a particular application and the present disclosure.

As will be appreciated by one of skill in the art, the herewith-described linear actuator (and any of the linear actuators referenced herewith) can be implemented with a wide variety of actuators available in the art. For example, in certain embodiments, the linear actuator will include one or more of a rack and pinion apparatus, an Acme screw and Acme nut; a ballscrew apparatus; a linear stepping motor; a transverse complementary ramps; a pneumatic cylinder; a pneumatic bladder; a pneumatic bellows; a hydraulic cylinder; a hydraulic bladder; a hydraulic bellows; a scissors linkage mechanism, including, for example, a scissors linkage mechanism linkage operated by a lead screw, a cylinder, or any of the other actuators discussed herewith, or any other appropriate actuator; a sarrus linkage mechanism; a thermoelectric actuator; a shape memory alloy actuator; a cable and pulley arrangement; as well as any of a wide variety of manual actuators such as, for example, a handcrank and/or a ratchet lever; a compressive spring; a tension spring; a torsion spring; an assembly of leaf springs; a spring including a plurality of Belleville washers; or any other linear actuator currently known, or that becomes known in the art, that is suited to the requirements of a particular application and to providing the requisite extension function.

Thus for example, in certain embodiments of the invention, the linear actuator will include one or more of an electrical solenoid, a pneumatic cylinder, hydraulic cylinder, a pneumatic bladder, a hydraulic bladder, a linear electric motor, linear stepping motor, a rotary actuator along with: an Acme screw and nut, a lead screw, a ballscrew, a cable, a pulley, a timing belt, a timing pulley, an appropriately sized worm gear reducer, a rack and pinion assembly, a rack and worm gear assembly, a piezoelectric actuator, a piezoelectric actuator combined with a ratchet and pawl driver, a spring loaded actuator, an actuator including a shape metal alloy, and any other appropriately functioning actuator component that is known or becomes known in the art.

Before or after adjustment, the patient is optionally secured to the patient interface panel 238 by employing one or more safety features, e.g., 260. Safety feature 260 includes, for example, a strap or belt, a locking bar disposed behind the patient's back, a hook and loop (e.g., Velcro™) interface between the table and one or more straps or garments worn by the patient in advance and including corresponding hook and loop elements. It will be appreciated by one of skill in the art that, in certain embodiments one or more safety features are engaged as soon as the patient steps onto the step. In other embodiments, a safety feature will be engaged after positioning of the patient is complete.

Figure 3A:
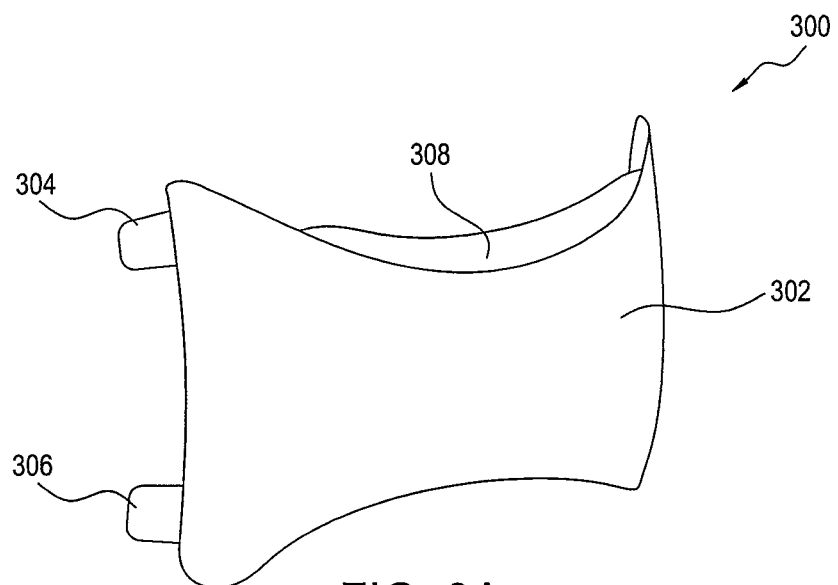
FIG. 3A shows, in schematic perspective view, certain features of a CBBCT imaging system prepared according to principles of the invention, including a safety device.
Figure 3B:
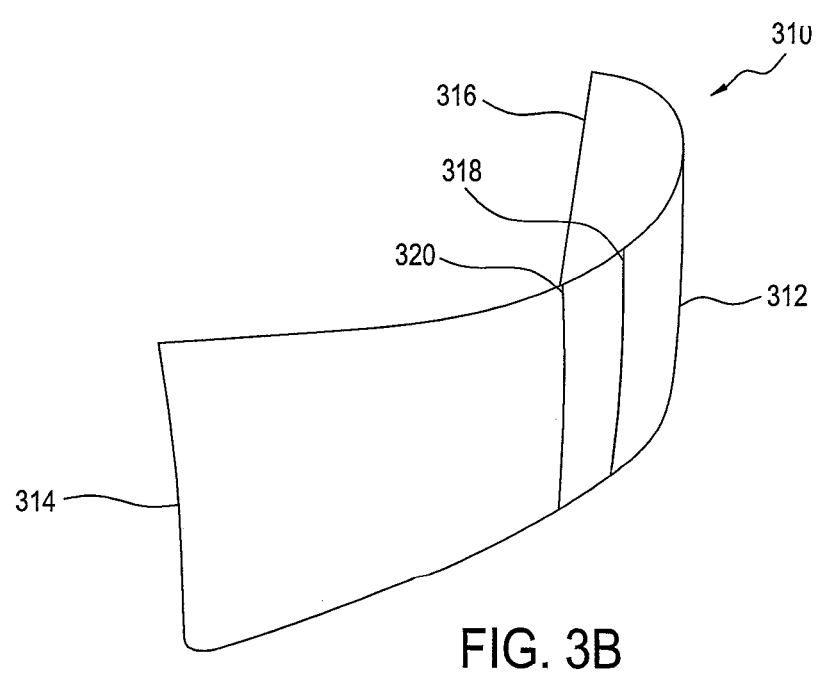
FIG. 3B shows, in schematic perspective view, additional features of a CBBCT imaging system prepared according to principles of the invention, including a further safety device.

FIGS. 3A and 3B show, in schematic perspective view, safety elements exemplary of safety feature 260 of CBBCT imaging system 200.

FIG. 3A shows a safety belt 300 for a CBBCT imaging system. Safety belt 300 includes a generally flexible member 302. In the illustrated embodiment, flexible member 302 includes, for example, a textile material such as, for example, a woven textile material, a knitted textile material, a felted textile material, or a chain-linked textile material. In other embodiments of the invention, the flexible member 302 includes one or more of a molded elastomeric polymer, a spray-formed elastomeric polymer a rope or cable, a natural material such as a natural polymer, a leather, a vegetable material, or other material or combination of materials appropriate to the objectives and functions described herewith.

The illustrated safety belt 300 includes a coupling mechanism e.g., 304, 306 adapted for detachably coupling the safety belt 300 to the patient support panel 238. In various embodiments of the invention, the coupling mechanism 304, 306 will include one or more of a buckle, a button, a hook and loop fastener, a mechanical snap fastener, a magnet fastener, an adhesive fastener, or any other fastener appropriate to the purposes in light of the present disclosure that is known or becomes known in the art, as well as combinations of the same.

In certain embodiments of the invention, the safety belt 300 will include a cushion element 308. In certain embodiments, the cushion element will include a generally elastic element that serves to distribute forces across an inner surface of the flexible element 302, operative to avoid excessive pressure at points of contact with the patient's back.

In certain embodiments of the invention, the cushion element 308 will include an expanding element such as for example, an air bladder, a liquid bladder, or a mechanical actuator. In certain embodiments of the invention, the expanding element is adapted to expand in a controlled fashion once the safety belt is coupled to the patient interface panel 238, thereby urging the patient against the patient interface surface 240.

FIG. 3B shows an alternative safety belt 310 for a CBBCT imaging system. Like safety belt 300, safety belt 310 includes a generally flexible member 312. In the illustrated embodiment, flexible member 312 includes, for example, a textile material and/or any of the materials provided as examples above.

The flexible member 312 has a first end 314 and a second end 316 that are adapted to be coupled to respective regions of patient interface panel 238. In certain embodiments of the invention, the respective ends 314 and 316 are substantially permanently coupled to the patient interface panel 238. In other embodiments of the invention, ends 314 and 316 are removably and/or adjustably coupled to the patient interface panel 238.

In the illustrated embodiment, the flexible member 312 has third 318 and fourth 320 internal ends that are adapted to be releasably coupled to each other. Accordingly, internal ends 318, 320 will include respective complementary coupling features. Thus, for example, internal ends 318, 320 will include respective complementary portions of a buckle, a button, a hook and loop fastener, a mechanical snap fastener, a magnet fastener, or any other fastener appropriate to the purposes in light of the present disclosure that is known or becomes known in the art, as well as combinations of the same.

In certain embodiments of the invention, the safety belt 300, 310 will include, for example, a polymer material such as, for example, polyamide, or polyaramid.

In other embodiment of the invention, the safety belt 300, 310, including elements of its assembly, will include one or more of polyethylene, polypropylene, polybutylene, polystyrene, polyester, acrylic polymers, polyvinylchloride, polyamide, or polyetherimide like ULTEM.®; a polymeric alloy such as Xenoy.® resin, which is a composite of polycarbonate and polybutyleneterephthalate or Lexan.® plastic, which is a copolymer of polycarbonate and isophthalate terephthalate resorcinol resin (all available from GE Plastics), liquid crystal polymers, such as an aromatic polyester or an aromatic polyester amide containing, as a constituent, at least one compound selected from the group consisting of an aromatic hydroxycarboxylic acid (such as hydroxybenzoate (rigid monomer), hydroxynaphthoate (flexible monomer), an aromatic hydroxyamine and an aromatic diamine, polyesterimide anhydrides with terminal anhydride group or lateral anhydrides.

In addition, any polymeric composite such as engineering prepregs or composites, which are polymers filled with pigments, carbon particles, silica, glass fibers, conductive particles such as metal particles or conductive polymers, or mixtures thereof may also be used. For example, a blend of polycarbonate and ABS (Acrylonitrile Butadiene Styrene) may be used.

Referring again to FIG. 2A, the exemplary patient interface panel 238 also includes one or more handles, e.g., 262. The handles are positioned and configured such that a patient is able to grasp the handles during mounting and operation of the CBBCT imaging system 200. This improves the ability of the patient to position their body on the patient interface panel, and provides stability to the patient during reorientation of the vertical plane gantry subsystem 202 as it pivots about hinge element 217, as will be further described below. In addition, grasping the handles will allow the patient to maintain stasis during imaging, resulting in improved data/image quality.

In various embodiments of the invention, the handles 262 will be adjustable in one or more of the dimensions of a centerline of the patient interface panel 238, and in a transverse dimension of that centerline, as well as in rotary fashion about a respective vertical axis disposed through the respective handle generally normal to surface 240 of the patient interface panel 238. The reader will appreciate that the illustrated location and configuration of the exemplary handle presented here is only one of many possible locations and configurations. Further descriptions of exemplary handles are provided below in relation to FIG. 4A-4E.

Accordingly, any of the handles described below in relation to FIGS. 4A-4E should be understood to exemplify possible handles to be employed in relation to CBBCT imaging system such as imaging system 200, along with other handles suitable to the application.

Figure 4A:
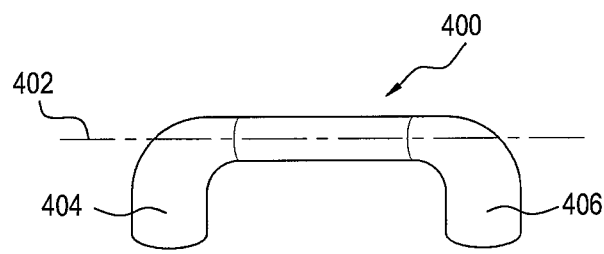
FIG. 4A shows, in schematic perspective view, certain features of a CBBCT imaging system prepared according to principles of the invention, including an exemplary handle.

FIGS. 4A-4E show, in schematic perspective view, exemplary handles that will be employed in respective embodiments of the invention. One of skill in the art will readily appreciate the advantages of the particular handle shown, and of others that are suggested by the present disclosure, and are deemed to be within its scope. For example, FIG. 4A shows a handle 400 adapted to be grasped primarily about a transverse longitudinal axis 402 and to be substantially fixedly coupled to a patient support panel, directly or through an adjustment apparatus at first 404 and second 406 ends thereof. It will be noted that the handle of FIG. 4A bear some similarity to the handles shown as elements 730, 732 in FIG. 7.

Figure 4B:
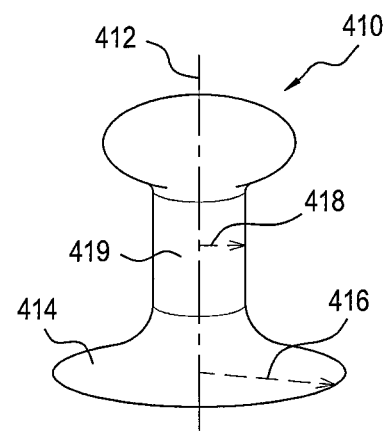
FIG. 4B shows, in schematic perspective view, additional features of a CBBCT imaging system prepared according to principles of the invention, including an exemplary handle.

FIG. 4B shows an alternative handle 410 adapted to be grasped primarily about a longitudinal axis 412 disposed generally normal to a surface of the patient support panel. A flange portion 414 of the handle 410 has a generally larger radius 416, than a radius 418 of a grip portion 419. This extended flange provides for effective coupling to the patient support panel, as well as improved stability and rigidity of the handle 410.

Figure 4C:
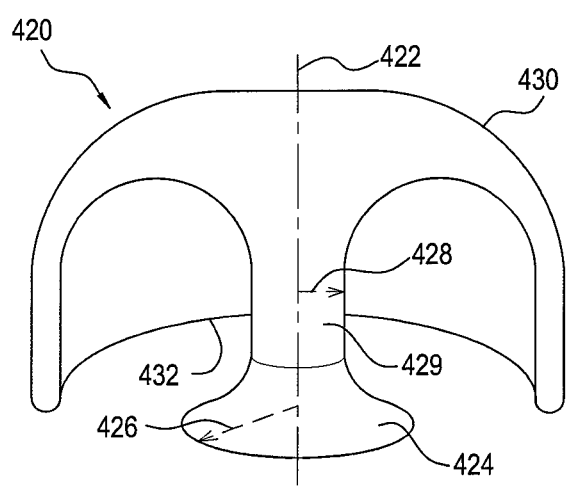
FIG. 4C shows, in schematic perspective view, still further features of a CBBCT imaging system prepared according to principles of the invention, including an exemplary handle.

FIG. 4C shows a further alternative handle 420 adapted to be grasped primarily about a longitudinal axis 422 disposed generally normal to a surface of the patient support panel. A lower flange portion 424 of the handle 420 has a generally larger radius 426, than a radius 428 of a grip portion 429. An upper flange portion 430 is disposed in arcuate fashion away from the longitudinal axis 422, and downward towards the table member to which it couples at a lower edge 432 thereof. The extended lower and upper flanges provide for effective coupling of the handle 420 to the patient support panel, as well as improved stability and rigidity of the handle.

Figure 4D:
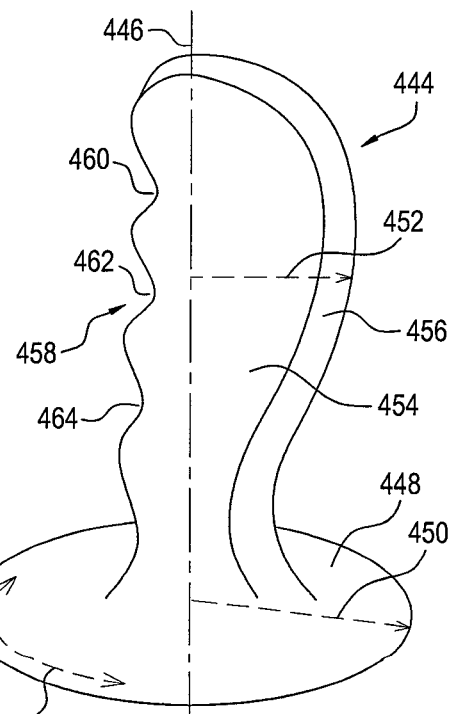
FIG. 4D shows, in schematic perspective view, yet other features of a CBBCT imaging system prepared according to principles of the invention, including an exemplary handle.

FIG. 4D shows a further alternative handle 434 adapted to be grasped primarily about a bulbous upper surface 436 disposed generally parallel to a surface of the patient support panel and transverse to a longitudinal axis 438 of the handle 434. The longitudinal axis 438 is disposed generally normal to the surface of the patient support panel and, when in use, passes generally through the palm and/or the metacarpal phalangeal joints of the patient's hand. A circumferential recess 440 disposed below the bulbous upper surface 436 and generally transverse to longitudinal axis 438 is adapted to receive the tips of the patient's fingers therewithin, enhancing patient grip. A lower flange portion 442 of the handle 434 provides for effective coupling of the handle 434 to the patient support panel, as well as improved stability and rigidity of the handle.

Figure 4E:
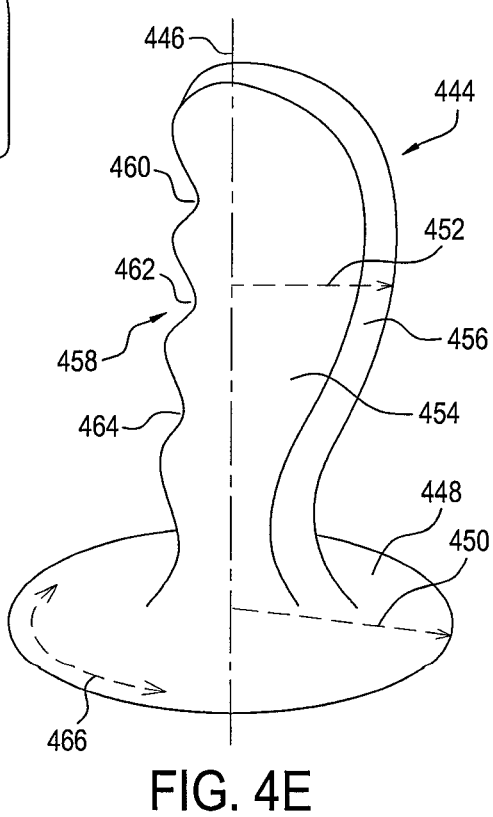
FIG. 4E shows, in schematic perspective view, still more aspects and features of a CBBCT imaging system prepared according to principles of the invention, including an exemplary handle.

FIG. 4E shows a further alternative handle 444 adapted to be grasped primarily about a longitudinal axis 446 disposed generally normal to a surface of the patient support panel. A lower flange portion 448 of the handle 444 has a generally larger radius 450, than a lateral dimension 452 of a grip portion 454. One vertical surface region 456 of the handle 444 is generally convex and adapted to be placed in contact with a palm of a patient.

The opposing vertical surface region 458 includes a plurality of concave recesses, e.g., 460, 462, 464, each adapted to receive a respective finger of the patient disposed therewithin. In certain embodiments, the handle 444 is substantially fixedly coupled a patient interface panel of the patient support panel. In other embodiments, the handle is coupled to the patient support panel through a rotary bearing and adapted to pivot circumferentially 466 substantially freely, or to be adjusted by pivoting circumferentially 466 and then releasably fixed in place, according to the requirements of a particular application of the invention. This pivotal motion allows adjustment of the position of surfaces 456 and 458 for optimum comfort of a patient grasping the handle.

Referring again to FIG. 2A, an exemplary CBBCT imaging system 200 includes a pivotal adjustment subsystem 264. In the exemplary embodiment of system 200, the pivotal adjustment subsystem 264 includes a drive portion 266, and a circumferential member 268. A first end 270 of the circumferential member 268 is substantially fixedly coupled to the structural member 214. A second end of the circumferential drive member 268 is disposed within, and operatively coupled to, a drive mechanism within the drive portion 266.

In operation, the drive mechanism of the drive portion 266 serves to retract 272 and extend 274 the circumferential member 268, thereby causing the structural member 214 (and the entire vertical plane gantry subsystem 202) to pivot about the hinge element 217.

Consequently, once a patient is properly positioned on the patient step 250, and secured against the patient interface surface region 240 of the patient interface panel 238, the vertical plane gantry subsystem 202 can be pivoted 276 about the hinge element 217. This tends to improve breast positioning within the x-ray beam 218, and to reduce patient fatigue that might otherwise result from standing during the imaging process.

Accordingly, FIG. 2B shows CBBCT imaging system 200 in a pivoted configuration. The circumferential member 268 has been retracted in direction 272 so that the vertical plane gantry subsystem 202 is disposed at an angle 278 of approximately 60° with respect to a generally horizontal upper surface region 280 of the foundation element 216.

It will be appreciated by one of skill in the art that, depending on the design details of a particular application or embodiment of the invention, it will be possible to pivot the vertical plane gantry subsystem 202 to an angle 278 of 45°, or anywhere down to and including zero. In addition, it will be evident that a negative angle positioning (i.e., patient head down) will also be available in corresponding embodiments of the invention. Accordingly, in respective embodiments of the invention, the vertical plane gantry subsystem will be positioned at an angle 278 within a range of from a least about 90° to at least about 80°; from at least about 80° to at least about 70°; from at least about 70° to at least about 60°; from at least about 60° to at least about 50°; from at least about 50° to at least about 40°; from least about 40° to at least about 30°; from at least about 30° to at least about 20°; at least about 20° to at least about 10°; from least about 10° to at least about 0°; from least about 0° to at least about −10°; release about −10° to at least about −20°.

In light of the foregoing, one of skill in the art will readily see that a wide variety of actuators will be employed in the drive mechanism of the drive portion 266. For example, in certain embodiments of the invention, the circumferential member 268 will include a rack portion and the drive mechanism will include a pinion gear coupled directly or indirectly to an electric motor. In other embodiments of the invention, the circumferential member 268 will include a rack portion and the drive mechanism will include a worm gear coupled directly or indirectly to an electric motor.

In still other embodiments of the invention, the circumferential member 268 and drive portion 266 will be replaced by any of a wide variety of linear actuators, including any of those exemplified and listed above in relation to other aspects of the invention.

In still other embodiments of the invention, additional mechanisms will be provided that allow pivotal adjustment of the vertical plane gantry subsystem 202 about, for example, a longitudinal axis 282, or about any other desired axis of rotation. The consequent additional degrees of freedom will permit the patient to be positioned in a spatial orientation that permits the subject breast to depend from the patient breast wall under the influence of gravity in a manner that optimizes imaging according to considerations of accommodating breast geometry, maintaining patient comfort and safety, improving image quality, limiting imaging duration and accommodating available imager dimensions and capacity, as well as imaging desirable chest wall features and managing direct and scattered x-ray exposure.

Thus, in certain embodiments of the invention, in addition to orienting the vertical plane gantry subsystem 202 about hinge 217, other orientation adjustments will be made, either automatically, according to preprogrammed parameters, or under manual control of medical or technical personnel, so as to provide one or more desirable positioning's and orientations of the breast within the CBBCT imaging system 200.

While the details of the additional mechanisms providing the additional degrees of freedom described above are omitted here for brevity, one of skill in the art will readily understand how such additional mechanisms would be provided and applied in light of the entirety of the present disclosure.

Figure 5A:
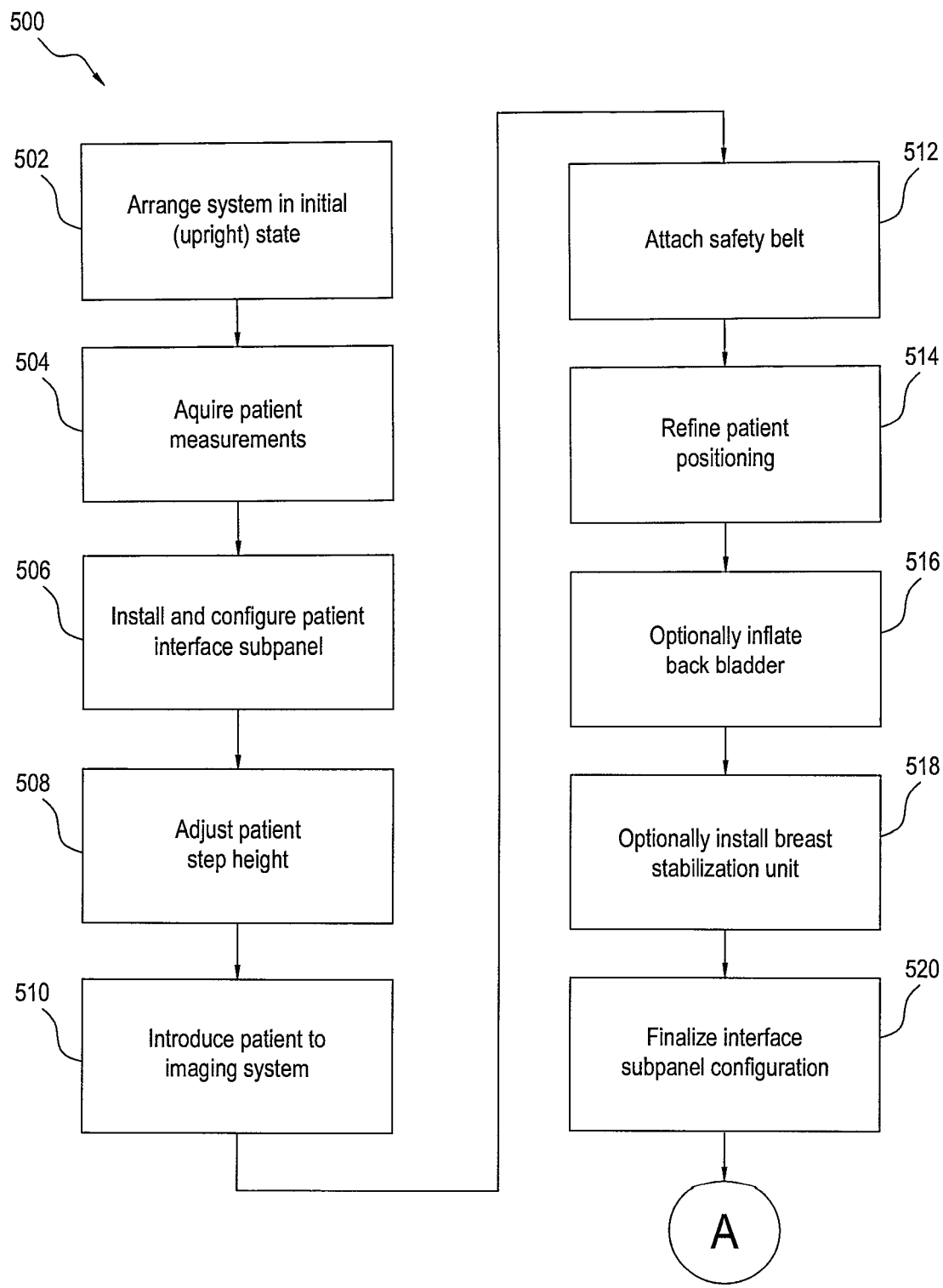
FIG. 5A shows, in functional block diagram form, certain aspects of processes and methods for using a CBBCT imaging system prepared according to principles of the invention.
Figure 5B:
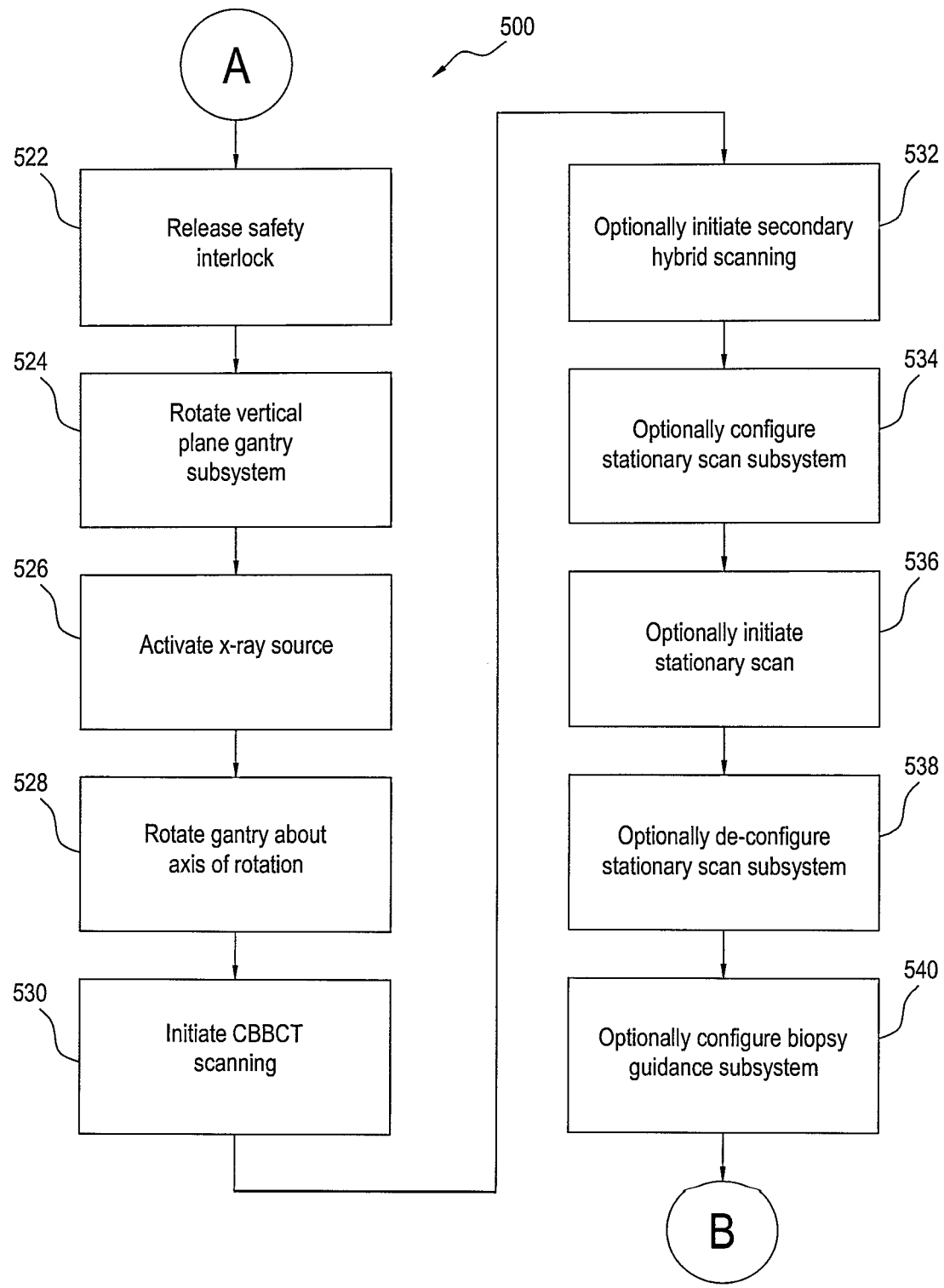
FIG. 5B shows, in functional block diagram form, further aspects of processes and methods for using a CBBCT imaging system prepared according to principles of the invention.
Figure 5C:
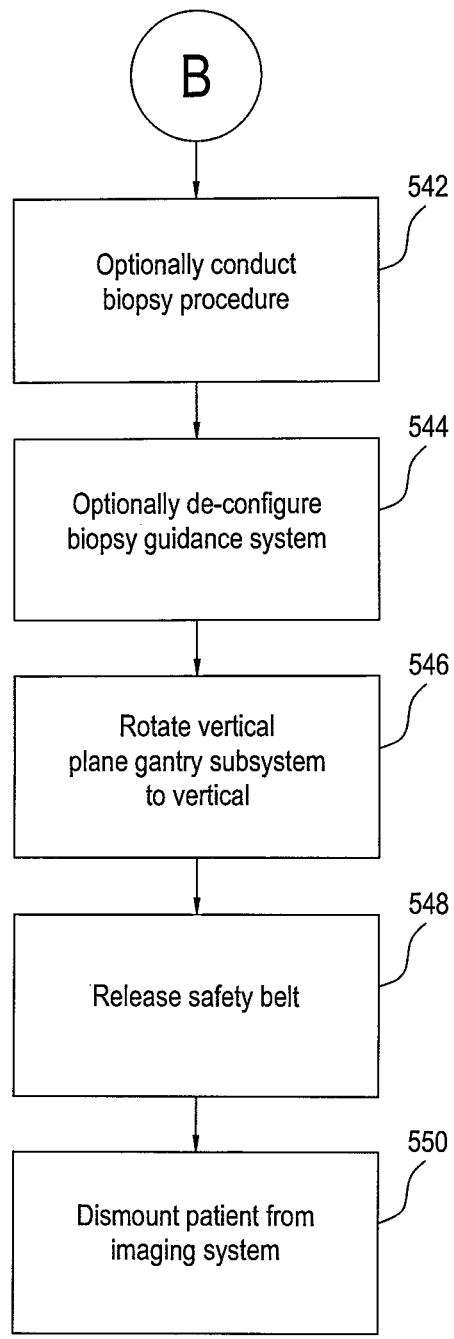
FIG. 5C shows, in functional block diagram form, additional aspects of processes and methods for using a CBBCT imaging system prepared according to principles of the invention.

FIGS. 5A-5C show, in functional block diagram form, processes and methods 500 for using a CBBCT imaging system according to principles of the invention. One of skill in the art will appreciate that the methods described herewith will be effectively employed along with any of the above-describe systems and with additional imaging systems and, in particular, with respect to CBBCT imaging system 200.

Accordingly, FIG. 5A illustrates the steps of arranging 502 a CBBCT imaging system in an initial (upright) state; capturing 504 patient measurements (i.e. body dimensions and characteristics); installing and configuring 506 a patient interface subpanel; adjusting 508 of patient step location; introducing 510 a patient to imaging system; attaching 512 or activating the patient safety device; further adjusting 514 patient positioning, including adjusting additional support system parameters (as further discussed below) to improve patient positioning for comfort and imaging; optionally inflating 516 the patient back bladder or otherwise activating the active cushion system towards the back of the patient so as to urge the patient against the patient interface panel and stabilize the patient against inadvertent movement; optionally installing 518 breast stabilization unit; further adjusting 520 patient interface subpanel configuration; releasing 522 safety interlock; rotating 524 vertical plane gantry subsystem about hinge element; activating 526 the x-ray source; rotating 528 the vertical plane gantry about the axis of rotation; and initiating 530 CBBCT scanning.

In addition to the steps indicated above, the methods and processes 500 will optionally include any one or more of the steps of: optionally initiating 532 secondary hybrid scanning such as, for example and without limitation, CBBCT/ultrasonic hybrid scanning, CBBCT/PET hybrid scanning, CBBCT/terahertz hybrid scanning, CBBCT/optical hybrid scanning; optionally configuring 534 a stationary scan subsystem and initiating 536 a stationary scan, as well as optionally de-configuring 538 the stationary scan subsystem; optionally configuring 540 a biopsy guidance subsystem, optionally conducting 542 a biopsy procedure, and optionally de-configuring 544 the biopsy guidance system. Of course one of skill in the art, having the benefit of the present disclosure will, in hindsight, appreciate that other optional steps combining available ancillary equipment and methods with the present method will be desirable and readily implemented. All of the foregoing, are therefore intended to be within the scope of the present disclosure.

The disclosed methods and processes further include the steps of rotating 546 the vertical scan gantry subsystem back to the initial (vertical) state; releasing 548 the safety device, including releasing relaxing any bladder or other active cushion system and releasing any safety belt; and dismounting 550 the patient from imaging system.

Figure 6:
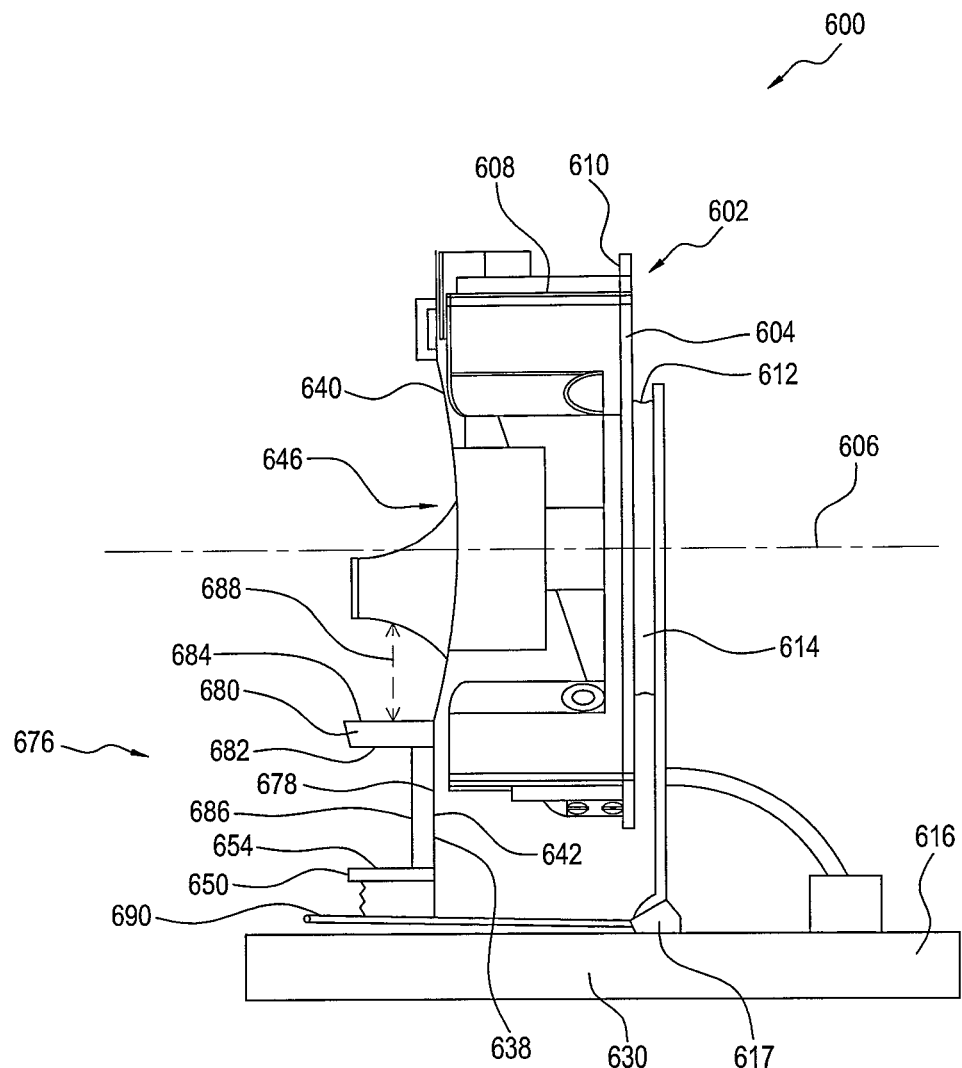
FIG. 6 shows, in schematic side elevation, additional aspects and configurations of an exemplary CBBCT imaging system, including a patient support saddle feature prepared according to principles of the invention.

FIG. 6 shows, in schematic side elevation, a portion of an exemplary CBBCT imaging system 600, similar to system 200, including a vertical plane gantry subsystem 602. The vertical plane gantry subsystem 602 includes a vertical plane gantry 604 configured to rotate about a generally horizontal axis of rotation 606.

Like systems 100 and 200 described above, system 600 includes an x-ray source 608. The exemplary x-ray source 608 is mounted on, and supported by, a mounting surface 610 of the vertical plane gantry 604. The vertical plane gantry 604 is supported by a bearing 612, and arranged for rotation about the axis of rotation 606. The bearing 612 is, in turn, coupled to and supported by a structural member 614, and the structural member 614 is pivotally coupled to, and supported by, a foundation element 616 of the vertical plane gantry subsystem 602 at a hinge element 617.

A base member 630 is coupled to the structural member 614. A patient interface panel 638 is coupled through the base member 630 to the structural member 614 so that the structural member 614 and the base member 630 serve to support the patient interface panel 638.

The patient interface panel 638 has a first patient interface surface region 640 and a second distal surface region 642, where the distal surface region 642 is disposed in spaced relation to the patient interface surface region 640. The exemplary patient interface panel 638 is similar in form and function to the patient interface panel 238 of FIG. 2.

Accordingly, referring to FIGS. 2 and 6 the patient interface panel includes an internal circumferential edge of the patient interface surface region. The internal circumferential edge circumscribes an aperture 646 through the patient interface panel 638 between patient interface surface region 640 and distal surface region 642.

In a manner similar to that described above, the patient interface surface region 640 is arranged to segregate the patient from the balance of the vertical gantry subsystem 602 with a breast of the patient disposed through the aperture 646. In various embodiments and aspects of the invention, a patient interface subsystem, as exemplified above, is disposed at the aperture 646. In various aspects, the patient interface subsystem will provide one or more of an aperture sized and located according to the particular patient and breast being imaged, shielding for regions of the patient that might otherwise be exposed to scattered x-ray photons, and support and stabilization of the breast being imaged, among other features.

The CBBCT imaging system 600 also includes an exemplary seat apparatus 676. In the illustrated embodiment, exemplary seat apparatus 676 is coupled to, and supported by, a corresponding portion 678 of the patient interface surface region 640. In other embodiments of the invention, the exemplary seat apparatus 676 is coupled to and supported by base portion 630, and/or patient step 650, or to any other location, feature or aspect of the CBBCT imaging system, or combination of the same, appropriate to the requirements of a particular application and embodiment of the invention.

The seat apparatus 676 includes a saddle portion 680 with a structural body member 682 a saddle upper surface region 684. Saddle upper surface region 684 is adapted to position and support a patient sitting astride the saddle portion 680 during imaging as well as during optional supplemental procedures.

In the illustrated embodiment, structural body member 682 is substantially fixedly coupled to an upper end of an exemplary seat column 686 which is coupled to the CBBCT imaging system 600 as described above, directly or through an appropriate positional adjustment apparatus. The seat column is optional, and in certain embodiments of the invention, the saddle structural body member is coupled directly to the CBBC to imaging system 600.

Accordingly, in certain embodiments of the invention, a lower end of the exemplary seat column 686 is operatively coupled to a seat adjustment mechanism. The seat adjustment a mechanism is coupled, directly or indirectly, to the base member 630 for support. Consequently, the weight of a patient seated on the saddle upper surface region 684 is transferred through the structural body member 682 of the saddle to the seat column 686, and from there through the seat adjustment mechanism to the base member 630.

In a desirable aspect of certain embodiments of the invention, the seat adjustment mechanism permits positional adjustment of the saddle portion 680 vertically 688 i.e., transverse to an upper surface 690 of the base member 630. In certain embodiments, the seat adjustment mechanism also permits pivotal rotations i.e., yaw of the saddle about a longitudinal axis of the seat column 686 and pitch about a transverse axis.

Beyond this, in certain embodiments of the invention, roll of the saddle portion 680 will also be adjustable to ensure comfort and optimal positioning of the patient with respect to the vertical plane gantry subsystem 602.

In a still further aspect of the invention, in certain embodiments the saddle will be removable or foldable, or otherwise displaceable so that a patient being imaged will not sit on the saddle, but will stand on an upper surface 654 of the step portion 650, for example. Accordingly, seating on the saddle will be available where desirable, but the saddle need not be employed where a standing mode of patient support is preferable.

As will be appreciated by one of skill in the art, the saddle portion 676 will be shaped and configured to promote optimal comfort and positioning of the patient with respect to the vertical plane gantry subsystem 602. In certain embodiments, the saddle portion 676 will include materials that advantageously are biocompatible and exhibit desirable characteristics of rheology and elastic durometer.

Accordingly, in respective embodiments of the invention, the saddle portion 676 will include materials appropriate to achieve these ends. A variety of exemplary materials corresponding to respective embodiments of the invention are provided above in relation to the description accompanying FIG. 3.

Figure 7:
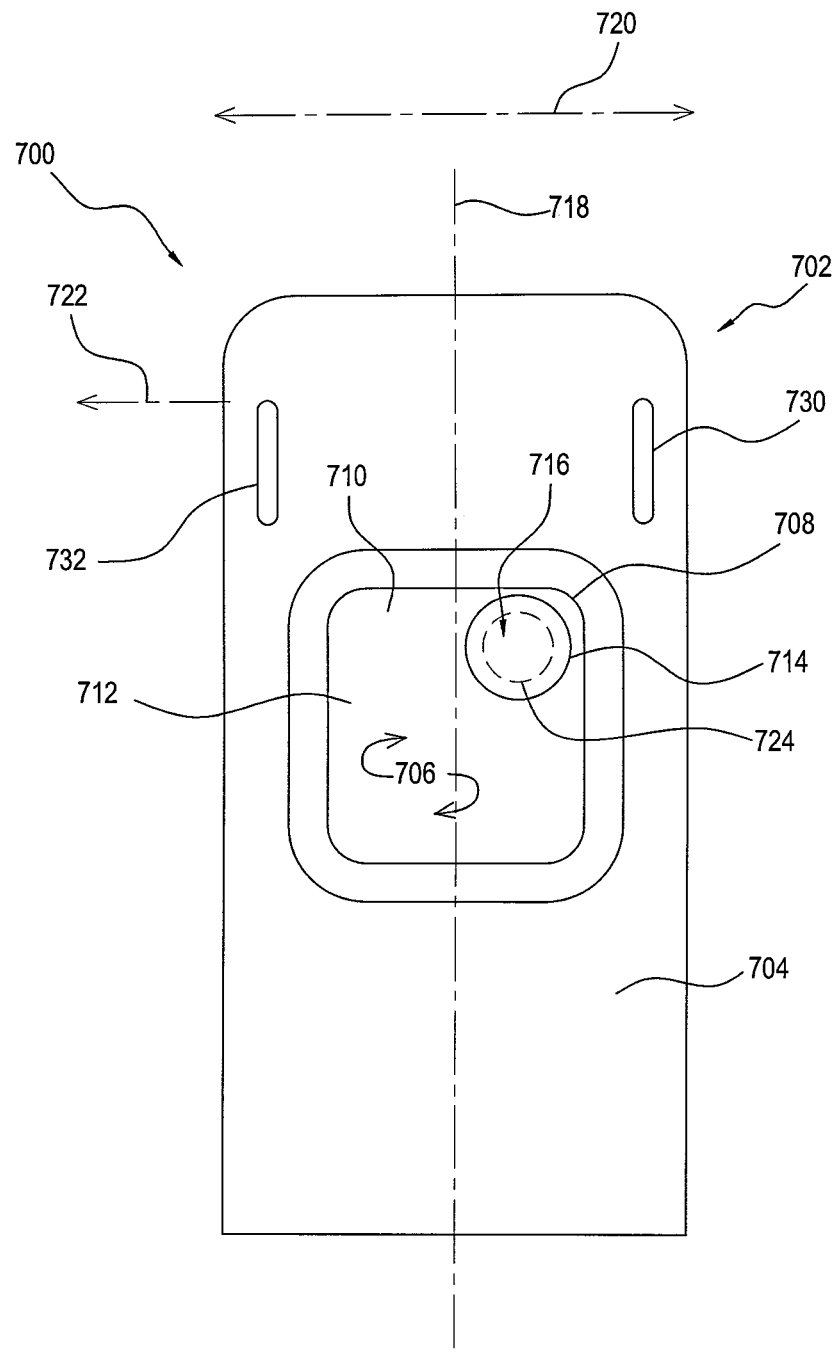
FIG. 7 shows, in schematic proximal elevation, certain features and of an exemplary CBBCT imaging system, including a patient interface panel, prepared according to principles of the invention.

FIG. 7 shows, in schematic proximal elevation, certain aspects of an exemplary CBBCT imaging system 700, including a vertical plane gantry subsystem 702, prepared according to principles of the invention. It will be appreciated that vertical plane gantry subsystem 702 is similar in its features to the subsystems discussed above and shows further aspects and details of the same invention, as well as additional inventive features and aspects. Accordingly, vertical plane gantry subsystem 702 includes a patient interface panel 704.

The patient interface panel 704 includes a patient interface surface region 706 adapted to support a patient during scanning. In various embodiments of the invention, the patient interface surface region 706 includes an inner circumferential edge 708 defining an aperture of the patient interface surface region through the patient interface panel 704. In some embodiments of the invention, the aperture is adapted to receive a breast of the patient disposed therethrough. In other embodiments, including that illustrated in FIG. 7, the aperture is adapted to receive a patient interface subpanel 710 that traverses circumferential edge 708. The patient interface subpanel 710 is coupled to and/or supported by the patient interface panel 704.

With respect to inner circumferential edge 708, it will be apparent that the particular shape of the circumferential edge will be selected in a corresponding embodiment so as to optimize considerations such as functionality and ease of manufacture. Accordingly, the geometry shown is merely exemplary of a wide variety of configurations that will be immediately apparent to one of skill in the art in light of the entirety of the present disclosure.

The patient interface subpanel 710 includes a subpanel surface region 712. A further inner circumferential edge 714 defines a subpanel aperture 716 through the subpanel. In the configuration illustrated, the subpanel aperture 716 is disposed to the right of a longitudinal centerline 718 of the patient interface panel 704. Accordingly, in typical operation of the CBBCT imaging system, a right breast of the patient will be disposed through the subpanel aperture 716 during imaging.

One of skill in the art will appreciate that, in certain embodiments of the invention, a plurality of subpanels will be provided that include apertures of different respective dimensions. For example, a subpanel having an internal circumferential edge 724 defining an aperture with a smaller diameter (as compared with illustrated aperture 716 defined by inner circumferential edge 714) will be available. Accordingly, technical or medical personnel will be able to select and install a subpanel having an aperture appropriate for the size of the breast of the particular patient to be imaged.

In other embodiments of the invention, the adjustment of aperture size will be effected by operation of an adjustment mechanism such as an iris leaf diaphragm aperture mechanism (see, e.g., FIGS. 9D-9F below). In certain embodiments the adjustment mechanism will be substantially permanently coupled to the patient interface panel 704 of the vertical plane gantry subsystem 702. In other embodiments of the invention, the adjustment mechanism will be coupled to a subpanel like subpanel 710 described above.

In certain embodiments of the invention, the aperture for receiving the breast to be imaged is disposed generally coincident with the centerline of the patient table. In such an embodiment, the patient will be positioned to align the breast to be imaged with the centerline of the table. Consequently, no additional transverse mechanism is required to align the breast with the axis of rotation of the gantry. It will be appreciated by one of skill in the art that this alignment of the breast aperture may be effected by providing the aperture directly in the patient table, or, alternately, in a subpanel configured for attachment or coupling to the patient table.

Figure 8:
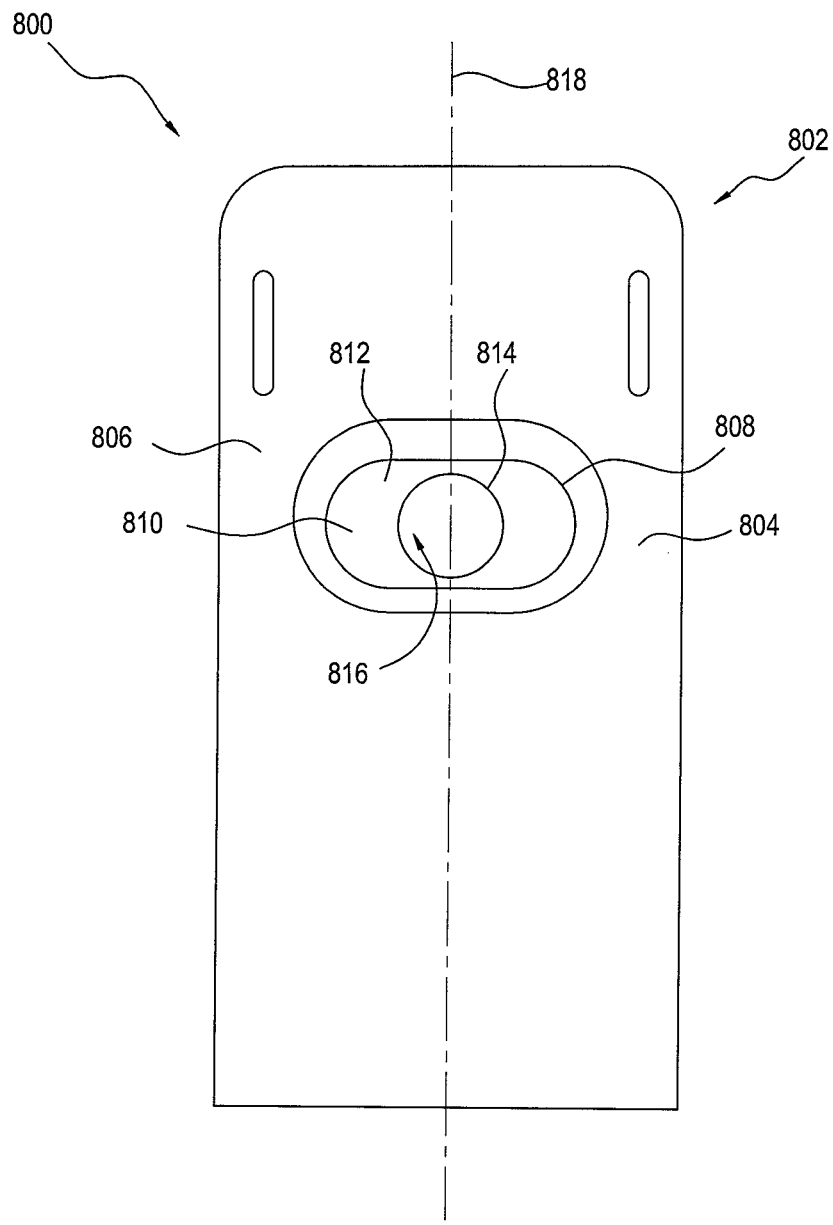
FIG. 8 shows, in schematic proximal elevation, additional features and of an exemplary CBBCT imaging system, including a patient interface panel, prepared according to principles of the invention.

Accordingly, FIG. 8 shows, in schematic proximal elevation, certain aspects of an exemplary CBBCT imaging system 800 including, including a vertical plane gantry subsystem 802, generally similar to vertical plane gantry subsystem 702 of FIG. 7. Vertical plane gantry subsystem 802 includes a patient interface panel 804.

The patient interface panel 804 includes a patient interface surface region 806 adapted to support a patient during scanning. In various embodiments of the invention, the patient interface surface region 806 includes an inner circumferential edge 808 defining an aperture of the patient interface surface region through 806 the patient interface panel 804. In some embodiments of the invention, the aperture is adapted to receive a breast of the patient disposed therethrough. In other embodiments, including that illustrated in FIG. 8, the aperture is adapted to receive a subpanel 810 that traverses circumferential edge 808. The subpanel 810 is coupled to and/or supported by the patient interface panel 804.

The subpanel 810 includes a subpanel surface region 812. A further inner circumferential edge 814 defines a subpanel aperture 816 through the subpanel. In the configuration illustrated, the subpanel aperture 816 is disposed coincident with a longitudinal centerline 818 of the patient interface panel 804. Accordingly, in typical operation of the CBBCT imaging system, either breast of the patient may be disposed through the subpanel aperture 816 during imaging, with the patient being arranged on the patient interface surface 806 of the patient interface panel 804 accordingly.

Although the inner circumferential edges 714, 724, 814 illustrated and discussed above are shown with substantially circular aspects, one of skill in the art will appreciate that the circumferential edge may be of any form considered advantageous according to the requirements of a particular application of the invention. Accordingly, in certain embodiments of the invention, circumferential edge will be generally elliptical, or may be generally triangular, or of any other regular or irregular polygonal form, or of any arcuate form or any combination of arcuate and linear segments, or any combination of the foregoing, all of which are considered to be within the scope of the present disclosure.

In the context of the foregoing discussions, FIGS. 9A-9F show, in schematic fashion, a variety of exemplary subpanel configurations that fall within the scope of the present invention and are similar to subpanels 710 and 810 described above in relation to FIGS. 7 and 8.

Figure 9A:
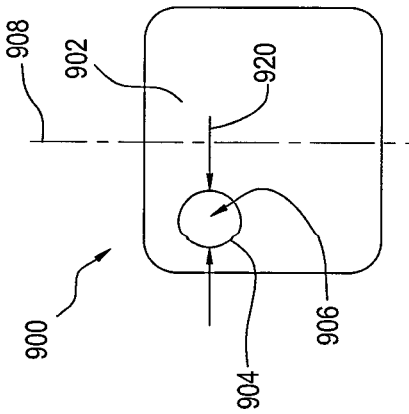
FIG. 9A shows, in schematic proximal elevation, certain features of a CBBCT imaging system prepared according to principles of the invention, including exemplary subpanel elements.
Figure 9B:
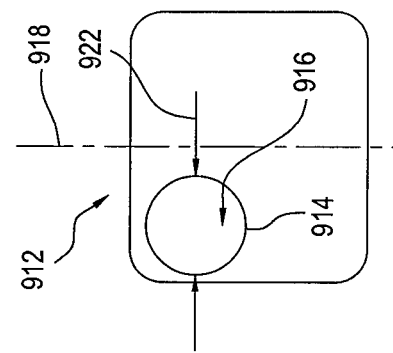
FIG. 9B shows, in schematic proximal elevation, additional aspects of a CBBCT imaging system prepared according to principles of the invention, including exemplary subpanel elements.
Figure 9C:
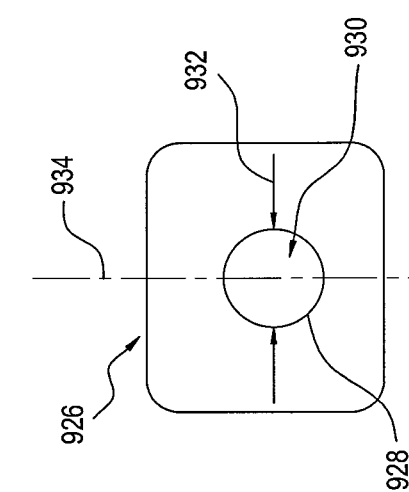
FIG. 9C shows, in schematic proximal elevation, further exemplary aspects of a CBBCT imaging system prepared according to principles of the invention, including exemplary subpanel elements.

FIGS. 9A-9C show respectively, in schematic elevation, exemplary subpanels having a variety of aperture locations and sizes.

Referring first to FIG. 9A, subpanel 900 includes a subpanel surface region 902. An inner circumferential edge 904 defines a subpanel aperture 906 through the subpanel. Consistent with the discussion above, the aperture 906 is adapted to receive a patient breast to be imaged therethrough. In the configuration illustrated, the subpanel aperture 906 is disposed to the left of a longitudinal centerline 908 of the subpanel 900. Accordingly, in typical operation of the CBBCT imaging system, a left breast of the patient will be disposed through the subpanel aperture 906 during imaging.

FIG. 9B shows a subpanel 912 similar to subpanel 900. As with subpanel 900, subpanel 912 has an inner circumferential edge 914 that defines a subpanel aperture 916 through the subpanel 912. Like aperture 906, aperture 916 is disposed to the left of a longitudinal centerline 918 of the subpanel 912. However, aperture 906 has a diameter 920 that is relatively smaller than the corresponding diameter 922 of aperture 916.

FIG. 9C shows a subpanel 926 similar to subpanels 900 and 912. As with subpanel 900, subpanel 926 has an inner circumferential edge 928 that defines a subpanel aperture 930 through the subpanel 926. Like aperture 906, aperture 930 has a diameter 932 that is substantially equal to corresponding diameter 922 of aperture 916. However, a centroid of aperture 930 is disposed substantially coincident with centerline 934 of the subpanel 926. Accordingly, whereas apertures 906 and 916 are primarily configured for receiving a left breast of the patient for imaging, aperture 930 is well adapted to receiving either a left breast or a right breast.

It will also be appreciated by one of skill in the art that, where appropriate perimeter configurations and coupling features are provided, symmetries of the illustrated panels will be used in respective embodiments of the invention to image, for example, either a left breast or a right breast by symmetric rotation of subpanel 900 or 912 about centerlines 908 and 918 respectively.

Likewise, rotation of the panels about an axis transverse to the centerlines can be used to locate the illustrated apertures relatively higher or lower respectively, according to the needs of a taller or shorter patient.

In light of the foregoing discussion, it will be appreciated by the reader that, in certain embodiments of the invention, a plurality of subpanels will be provided along with an imaging system, such that the subpanel with the appropriate aperture will be selected according to the height, weight, breast size and other parameters of the patient.

In another aspect embodiment of the invention, individual reusable subpanels will be purchased so as to be available where required. In still other embodiments of the invention, disposable subpanels will be employed for single use with a respective patient, and thereafter discarded.

Figure 9D:
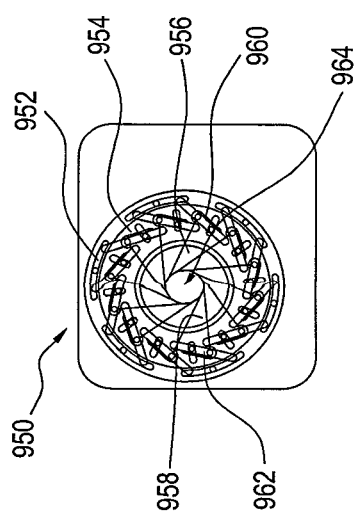
FIG. 9D shows, in schematic proximal elevation, certain features of a CBBCT imaging system prepared according to principles of the invention, including exemplary adjustable subpanel elements.
Figure 9E:
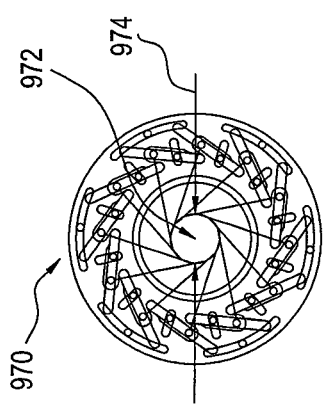
FIG. 9E shows, in schematic proximal elevation, further details of a CBBCT imaging system prepared according to principles of the invention, including exemplary adjustable subpanel elements.
Figure 9F:
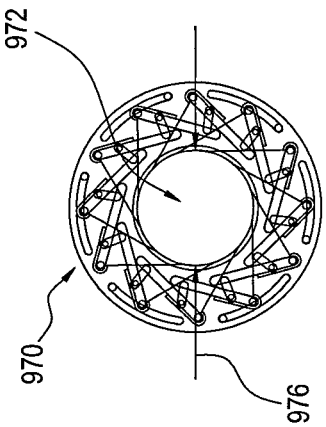
FIG. 9F shows, in schematic proximal elevation, additional configurations of a CBBCT imaging system prepared according to principles of the invention, including exemplary adjustable subpanel elements.

FIGS. 9D-9F show schematic representations of a further subpanel 950 prepared according to principles of the invention. Subpanel 950 is shown in cutaway view, and illustrates an adjustment mechanism 952 included in subpanel 950.

In the exemplary embodiment illustrated, adjustment mechanism 952 includes a mechanical iris mechanism 954. The adjustable iris mechanism 954 includes a plurality of leaf elements, e.g., 956, 958 respectively coupled to corresponding operative links 960, 962. One of skill in the art will recognize the adjustable iris mechanism 954 as similar in form and function to iris mechanisms employed in photographic cameras. Accordingly, by operation of the operative links 960, 962, the leaf elements 956, 958 will be urged to pivot so as to adjust a diameter of an aperture 964 to a preferred value according to the requirements for imaging a particular patient breast.

By way of further illustration, in FIG. 9E exemplary iris mechanism 970 is adjusted and configured to present an aperture 972 having a relatively small diameter 974. In FIG. 9F, exemplary iris mechanism 970 is adjusted and configured to present the same aperture 972 with a relatively large diameter 976.

Figure 10:
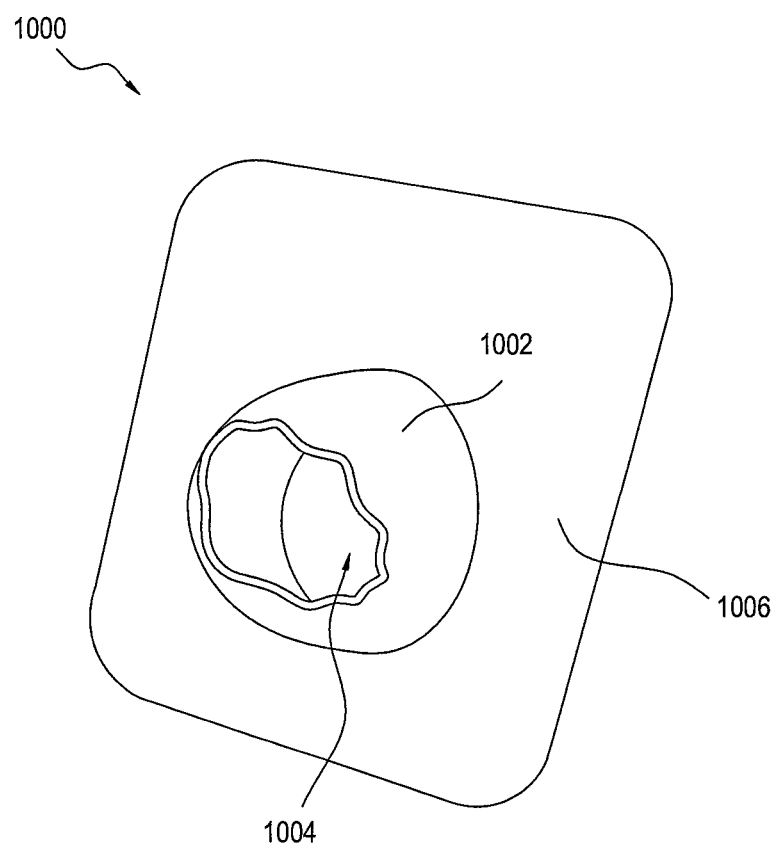
FIG. 10 shows, in distal schematic perspective view, certain further features of a CBBCT imaging system prepared according to principles of the invention, including exemplary breast stabilization features.

In a still further aspect of the invention FIG. 10 shows, in schematic distal cutaway perspective view, a subpanel 1000 including a breast stabilizer unit 1002 adapted and configured to support and stabilize a patient breast during imaging. As illustrated, the breast stabilizer unit 1002 is coupled to the subpanel 1000 at aperture 1004 of distal surface 1006.

In certain applications, the stabilizer unit 1002 is configured and adjusted to maintain an approximate geometric centroid of the breast coincident with an axis of rotation (e.g., 206 of FIG. 2A) and longitudinal axis 220 of the x-ray beam 218. It will be appreciated by one of skill in the art, however, that any of a wide variety of placements and configurations of the breast will be desirable in respect to a particular patient, application, or imaging objective, and will be achieved by an appropriate configuration, shape, and placement of the stabilizer unit 1002.

Accordingly, the stabilizer unit 1002 is arranged, adapted and configured to support, stabilize and hold in place, at least a portion of breast, with respect to the above-described transit path 228 of flat panel detector receiving surface 226, during imaging of the breast by the imaging system.

One of skill in the art will readily appreciate the various benefits and modalities for employing a breast stabilizer unit like the exemplary stabilizer unit presented herewith upon review of the related applications listed above.

In certain embodiments of the invention, the CBBCT scanning system comprises a foundation element and a vertical plane gantry subsystem coupled to and supported by the foundation element. The vertical plane gantry subsystem includes a CBBCT gantry that is adapted and configured to rotate about a generally horizontal axis of rotation. The vertical plane gantry subsystem also includes a patient interface panel, the patient interface panel has a patient interface surface region with an aperture therethrough. A patient interface sub-panel may be disposed within the aperture of the patient interface panel.

Also included is a pivotal adjustment subsystem which includes a pivotal hinge mutually coupled between the foundation element and the vertical plane gantry subsystem. The pivotal hinge is adapted to rotate the patient interface panel from a first generally vertical orientation to a second generally non-vertical orientation.

In certain embodiments of the invention, the pivotal adjustment subsystem of the CBBCT scanning system further comprises an actuator, the actuator being adapted to control the rotation of the first patient interface panel.

In certain embodiments of the invention, the actuator comprises a linear actuator, the linear actuator having a first end operatively coupled to the foundation element and a second end operatively coupled to the vertical plane gantry subsystem.

In some embodiments of the invention, the patient interface panel of the CBBCT scanning system includes a patient support saddle portion.

In certain embodiments of the invention, the saddle portion is coupled to a seat adjustment mechanism.

In certain embodiments of the invention, the seat adjustment mechanism is adapted to adjust a saddle upper surface of the saddle portion in a vertical degree of freedom, while in some embodiments of the invention the seat adjustment mechanism is adapted to adjust a saddle upper surface of the saddle portion in a horizontal degree of freedom.

In certain embodiments of the invention, the seat adjustment mechanism is adapted to adjust a saddle upper surface of the saddle portion in at least one of a pitch degree of freedom, a roll degree of freedom, and a yaw degree of freedom.

In certain embodiments of the invention, the patient interface sub-panel of the CBBCT scanning system includes a breast aperture, the breast aperture being adapted to receive a patient breast therethrough for imaging.

In certain embodiments of the invention, the breast aperture includes an aperture adjustment mechanism, the aperture adjustment mechanism is adapted to change a diameter of the aperture, whereby the diameter will be adjusted according to a size of a patient breast.

In certain embodiments of the invention, the patient interface sub-panel of the CBBCT scanning system includes a breast stabilization unit to support a patient breast during imaging.

In certain embodiments of the invention a method of conducting a CBBCT scan comprises providing a foundation element with a generally horizontal upper surface region and a vertical plane gantry subsystem pivotally coupled to the foundation element. The vertical plane gantry subsystem has a patient step portion with a patient step upper surface region to support a patient during imaging.

The method also includes providing a pivotal adjustment subsystem mutually coupled between the foundation element and the vertical plane gantry subsystem, disposing the imaging system in a first substantially vertical configuration with respect to the generally horizontal upper surface region of the foundation element, adjusting the patient step portion for patient positioning, introducing the patient to the patient step upper surface in a standing posture, securing a safety feature to maintain patient positioning with respect to the vertical plane gantry subsystem, positioning a patient breast within an imaging aperture of the vertical plane gantry subsystem, activating the pivotal adjustment subsystem, rotating the imaging system from the first substantially vertical configuration into a second substantially non-vertical configuration with respect to the generally horizontal upper surface region of the foundation element and CBBCT scanning the patient breast with the vertical plane gantry subsystem.

The method further includes rotating the imaging system from the second substantially non-vertical configuration to the first substantially vertical configuration, releasing the safety feature and dismounting the patient from the patient step upper surface region of the patient step portion.

In certain embodiments of the invention the method of conducting a CBBCT scan further comprises the steps of installing a patient support subpanel at the subpanel aperture of the patient interface panel of the vertical plane gantry subsystem and disposing the patient breast through a breast aperture of the patient support subpanel.

In certain embodiments of the invention the method of conducting a CBBCT scan further comprises the steps of receiving a patient parameter value and selecting the patient support subpanel according to the patient parameter value.

In some embodiments of the invention selecting the patient support subpanel according to the patient parameter value of the patient further comprises the step of selecting a patient support subpanel having a breast aperture diameter corresponding to a breast diameter value of the patient, while in still further embodiments selecting the patient support subpanel further comprises selecting a patient support subpanel having a breast aperture beneficially disposed to one side of a centerline of the patient interface panel.

In certain embodiments of the invention the method of conducting a CBBCT scan comprises adjusting a diameter of the breast aperture of the patient support subpanel.

In certain embodiments of the invention the method of conducting a CBBCT scan comprises disposing a patient breast through the breast aperture of the patient support subpanel and further comprises positioning the patient breast within a breast stabilization unit of the patient interface panel.

In certain embodiments of the invention activating the pivotal adjustment subsystem during conduction of a CBBCT scan further comprises the step of manually motivating the pivotal adjustment subsystem while in still further embodiments activating the pivotal adjustment subsystem comprises energizing an electric motor within the pivotal adjustment subsystem and operating the electric motor to extend a linear actuator member of the pivotal adjustment subsystem.

In some embodiments of the invention activating the pivotal adjustment subsystem comprises energizing an electric motor within the pivotal adjustment subsystem and operating the electric motor to extend a linear actuator member of the pivotal adjustment subsystem.

In some embodiments of the invention activating the pivotal adjustment subsystem comprises activating a pneumatic cylinder of the pivotal adjustment subsystem while in still further embodiments of the invention activating the pivotal adjustment subsystem further comprises the step of releasing a safety interlock of the pivotal adjustment subsystem.

In certain embodiments of the invention the method of conducting a CBBCT scan further comprises adjusting a position of a saddle portion of the vertical plane gantry subsystem while in some embodiments of the invention the method of conducting a CBBCT scan further comprises seating a patient on a saddle portion of the vertical plane gantry subsystem.

In certain embodiments of the invention the method of conducting a CBBCT scan includes providing a foundation element with a generally horizontal upper surface region and a vertical plane gantry subsystem pivotally coupled to the foundation element. The vertical plane gantry subsystem has a patient step portion with a patient step upper surface region adapted to support a patient during imaging. The imaging system is disposed in a first substantially vertical configuration with respect to the generally horizontal upper surface region of the foundation element and the patient step portion is adjusted for patient positioning.

The method includes introducing the patient to the patient step upper surface in a standing posture, positioning a patient breast within an imaging aperture of the vertical plane gantry subsystem, rotating the imaging system from the first substantially vertical configuration into a second substantially non-vertical configuration with respect to the generally horizontal upper surface region of the foundation element and CBBCT scanning the patient breast with the vertical plane gantry subsystem. The imaging system is rotated from the second substantially non-vertical configuration to the first substantially vertical configuration so the patient can dismount from the patient step upper surface region of the patient step portion.

While the exemplary embodiments described above have been chosen primarily from the field of apparatus, and corresponding systems and methods in the operation of a CBBCT imaging system, including ergonomically improved systems and methods thereof, one of skill in the art will appreciate that the principles of the invention are equally well applied, and that the benefits of the present invention are equally well realized in a wide variety of other imaging technologies, for example, imaging of other body parts and imaging of other subjects such as industrial and technological products. Further, while the invention has been described in detail in connection with the presently preferred embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Accordingly, the invention is not to be seen as limited by the foregoing description, but is only limited by the scope of the appended claims.

The invention claimed is:

1. A method of conducting a Cone Beam Breast Computed Tomography (CBBCT) scan comprising:
   providing a foundation element, said foundation element having a generally horizontal upper surface region;
   providing a vertical plane gantry subsystem pivotally coupled to said foundation element, said vertical plane gantry subsystem having a patient step portion, said patient step portion having a patient step upper surface region, said patient step upper surface region being adapted to support a patient during imaging;
   providing a pivotal adjustment subsystem mutually coupled between said foundation element and said vertical plane gantry subsystem;
   disposing said imaging system in a first substantially vertical configuration with respect to said generally horizontal upper surface region of said foundation element;
   adjusting said patient step portion for patient positioning;
   introducing said patient to said patient step upper surface in a standing posture;
   securing a safety feature to maintain patient positioning with respect to said vertical plane gantry subsystem;
   positioning a patient breast within an imaging aperture of said vertical plane gantry subsystem;
   activating said pivotal adjustment subsystem;
   rotating said imaging system from said first substantially vertical configuration into a second substantially non-vertical configuration with respect to said generally horizontal upper surface region of said foundation element;
   CBBCT scanning said patient breast with said vertical plane gantry subsystem;
   rotating said imaging system from said second substantially non-vertical configuration to said first substantially vertical configuration;
   releasing said safety feature; and
   dismounting said patient from said patient step upper surface region of said patient step portion;
   wherein said activating said pivotal adjustment subsystem further comprises the step of:
   activating a pneumatic cylinder of said pivotal adjustment subsystem.

2. A method of conducting a Cone Beam Breast Computed Tomography (CBBCT) CBBCT scan as defined in claim 1
   wherein said activating said pivotal adjustment subsystem further comprises the step of:
   releasing a safety interlock of said pivotal adjustment subsystem.

3. A method of conducting a Cone Beam Breast Computed Tomography (CBBCT) scan as defined in claim 1 further comprising the step of:
   adjusting a position of a saddle portion of said vertical plane gantry subsystem.

4. A method of conducting a Cone Beam Breast Computed Tomography (CBBCT) scan as defined in claim 1 further comprising the step of:
   seating a patient on a saddle portion of said vertical plane gantry subsystem.

5. A method of conducting a Cone Beam Breast Computed Tomography (CBBCT) scan as defined in claim 1 wherein said vertical plane gantry subsystem includes a patient interface panel, said patient interface panel having a subpanel aperture therethrough; and further comprising the steps of:
   installing a patient support subpanel at said subpanel aperture of said patient interface panel; and
   disposing said patient breast through a breast aperture of said patient support subpanel.

6. A method of conducting a Cone Beam Breast Computed Tomography (CBBCT) scan as defined in claim 5 further comprising the steps of:
   receiving a patient parameter value; and
   selecting said patient support subpanel according to said patient parameter value.

7. A method of conducting a Cone Beam Breast Computed Tomography (CBBCT) scan as defined in claim 6 wherein said selecting said patient support subpanel according to said patient parameter value of said patient further comprises the step of:
   selecting a patient support subpanel having a breast aperture diameter corresponding to a breast diameter value of said patient.

8. A method of conducting a Cone Beam Breast Computed Tomography (CBBCT) scan as defined in claim 6 wherein said selecting said patient support subpanel according to said patient parameter value of said patient further comprises the step of:
   selecting a patient support subpanel having a breast aperture beneficially disposed to one side of a centerline of said patient interface panel.

9. A method of conducting a Cone Beam Breast Computed Tomography (CBBCT) scan comprising:
   providing a foundation element, said foundation element having a generally horizontal upper surface region;
   providing a vertical plane gantry subsystem pivotally coupled to said foundation element said vertical plane gantry subsystem having a patient step portion, said patient step portion having a patient step upper surface region, said patient step upper surface region being adapted to support a patient during imaging;
   disposing said imaging system in a first substantially vertical configuration with respect to said generally horizontal upper surface region of said foundation element;
   adjusting said patient step portion for patient positioning;
   introducing said patient to said patient step upper surface in a standing posture;

positioning a patient breast within an imaging aperture of said vertical plane gantry subsystem;

rotating said imaging system from said first substantially vertical configuration into a second substantially non-vertical configuration with respect to said generally horizontal upper surface region of said foundation element;

CBBCT scanning said patient breast with said vertical plane gantry subsystem;

rotating said imaging system from said second substantially non-vertical configuration to said first substantially vertical configuration;

dismounting said patient from said patient step upper surface region of said patient step portion.

\* \* \* \* \*